(12) United States Patent
Benjamin et al.

(10) Patent No.: US 11,938,284 B2
(45) Date of Patent: Mar. 26, 2024

(54) CATHETER SYSTEM AND METHODS OF USING SAME

(71) Applicant: Endologix LLC, Irvine, CA (US)

(72) Inventors: Joshua Benjamin, Aliso Viejo, CA (US); Stefan Schreck, Fallbrook, CA (US)

(73) Assignee: Endologix LLC, Irvine, CA (US)

( * ) Notice: Subject to any disclaimer, the term of this patent is extended or adjusted under 35 U.S.C. 154(b) by 794 days.

(21) Appl. No.: 16/725,948

(22) Filed: Dec. 23, 2019

(65) Prior Publication Data
US 2020/0129739 A1    Apr. 30, 2020

Related U.S. Application Data

(63) Continuation of application No. 15/639,028, filed on Jun. 30, 2017, now Pat. No. 10,512,758, which is a
(Continued)

(51) Int. Cl.
*A61M 25/00* (2006.01)
*A61F 2/95* (2013.01)
(Continued)

(52) U.S. Cl.
CPC .......... *A61M 25/0662* (2013.01); *A61F 2/95* (2013.01); *A61M 25/0097* (2013.01);
(Continued)

(58) Field of Classification Search
CPC .......... A61M 25/0662; A61M 25/0097; A61M 2025/0006; A61M 2025/0079;
(Continued)

(56) References Cited

U.S. PATENT DOCUMENTS

| 4,960,412 A | 10/1990 | Fink |
| 5,098,395 A | 3/1992 | Fields |

(Continued)

FOREIGN PATENT DOCUMENTS

| WO | WO-2006/117321 A2 | 11/2006 |
| WO | WO-2007/027830 A1 | 3/2007 |

OTHER PUBLICATIONS

European Office Action dated Jul. 11, 2013, from application No. 12178965.5.

(Continued)

*Primary Examiner* — Steven O Douglas
(74) *Attorney, Agent, or Firm* — Foley & Lardner LLP

(57) ABSTRACT

Some embodiments are directed to a catheter system comprising an introducer having a main body, an introducer sheath projecting from the main body, and a first seal supported within the introducer and a catheter having a main body, an outer sheath projecting from the main body, a second seal supported within the catheter, and an inner core configured to be advanced axially through the main body, the second seal, and the outer sheath. The introducer can be configured to be selectively engageable with the catheter so that the catheter can be selectively and removably linked with the introducer in the axial direction. The catheter system can also be configured such that, when the introducer and the catheter are linked, the catheter can be rotatable relative to the introducer. The introducer can be configured to radially restrain an endoluminal prosthesis.

16 Claims, 18 Drawing Sheets

Related U.S. Application Data continuation of application No. 13/544,426, filed on Jul. 9, 2012, now Pat. No. 9,700,701, which is a continuation of application No. 12/496,446, filed on Jul. 1, 2009, now Pat. No. 8,216,295.

(60) Provisional application No. 61/184,742, filed on Jun. 5, 2009, provisional application No. 61/077,429, filed on Jul. 1, 2008.

(51) Int. Cl.
*A61M 25/06* (2006.01)
*A61F 2/966* (2013.01)

(52) U.S. Cl.
CPC ............ *A61F 2/9517* (2020.05); *A61F 2/966* (2013.01); *A61M 2025/0006* (2013.01); *A61M 2025/0079* (2013.01); *A61M 2025/0681* (2013.01)

(58) Field of Classification Search
CPC . A61M 2025/0681; A61F 2/95; A61F 2/9517; A61F 2/966
See application file for complete search history.

(56) References Cited

U.S. PATENT DOCUMENTS

| | | | |
|---|---|---|---|
| 5,137,519 A | 8/1992 | Littrell et al. | |
| 5,267,982 A | 12/1993 | Sylvanowicz | |
| 5,391,152 A | 2/1995 | Patterson | |
| 5,545,152 A | 8/1996 | Funderburk et al. | |
| 5,782,807 A | 7/1998 | Falvai et al. | |
| 5,782,817 A | 7/1998 | Franzel et al. | |
| 5,843,046 A | 12/1998 | Motisi et al. | |
| 5,885,217 A | 3/1999 | Gisselberg et al. | |
| 5,997,562 A | 12/1999 | Zadno-Azizi et al. | |
| 6,033,413 A | 3/2000 | Mikus et al. | |
| 6,123,723 A * | 9/2000 | Konya | A61F 2/07 606/108 |
| 6,146,415 A | 11/2000 | Fitz | |
| 6,183,443 B1 | 2/2001 | Kratoska et al. | |
| 6,197,016 B1 | 3/2001 | Fourkas et al. | |
| 6,254,609 B1 | 7/2001 | Vrba et al. | |
| 6,273,895 B1 | 8/2001 | Pinchuk et al. | |
| 6,592,581 B2 | 7/2003 | Bowe | |
| 6,607,551 B1 | 8/2003 | Sullivan et al. | |
| 6,641,564 B1 | 11/2003 | Kraus | |
| 6,652,492 B1 | 11/2003 | Bell et al. | |
| 6,808,509 B1 | 10/2004 | Davey | |
| 6,808,520 B1 | 10/2004 | Fourkas et al. | |
| 6,872,193 B2 | 3/2005 | Shaw et al. | |
| 7,096,554 B2 | 8/2006 | Austin et al. | |
| 7,413,560 B2 | 8/2008 | Chong et al. | |
| 7,481,805 B2 | 1/2009 | Magnusson | |
| 7,526,849 B2 | 5/2009 | Serrano | |
| 7,553,319 B2 | 6/2009 | Bagaoisan et al. | |
| 7,846,135 B2 | 12/2010 | Runfola | |
| 7,871,419 B2 | 1/2011 | Devellian et al. | |
| 7,871,430 B2 | 1/2011 | Pavcnik et al. | |
| 7,922,755 B2 | 4/2011 | Acosta et al. | |
| 7,942,924 B1 | 5/2011 | Perez et al. | |
| 8,025,692 B2 | 9/2011 | Feeser | |
| 8,216,295 B2 | 7/2012 | Benjamin et al. | |
| 8,844,430 B2 | 9/2014 | Mastropasqua et al. | |
| 2001/0049547 A1 | 12/2001 | Moore | |
| 2002/0019660 A1 | 2/2002 | Gianotti et al. | |
| 2002/0072712 A1 | 6/2002 | Nool et al. | |
| 2002/0123786 A1 | 9/2002 | Gittings et al. | |
| 2004/0044395 A1 | 3/2004 | Nelson | |
| 2004/0098084 A1 | 5/2004 | Hartley et al. | |
| 2004/0210239 A1 | 10/2004 | Nash et al. | |
| 2004/0215312 A1 | 10/2004 | Andreas | |
| 2004/0225344 A1 | 11/2004 | Hoffa et al. | |
| 2004/0230286 A1 | 11/2004 | Moore et al. | |
| 2005/0027345 A1 | 2/2005 | Horan et al. | |
| 2005/0038495 A1 | 2/2005 | Greenan | |
| 2005/0049667 A1 | 3/2005 | Arbefeuille et al. | |
| 2005/0049678 A1 | 3/2005 | Cocks et al. | |
| 2005/0060016 A1 | 3/2005 | Wu et al. | |
| 2005/0154441 A1 | 7/2005 | Schaeffer et al. | |
| 2005/0240255 A1 | 10/2005 | Schaeffer | |
| 2005/0246008 A1 | 11/2005 | Hogendijk et al. | |
| 2005/0273155 A1 * | 12/2005 | Bahler | A61F 2/07 623/1.13 |
| 2006/0018948 A1 | 1/2006 | Guire et al. | |
| 2006/0100658 A1 | 5/2006 | Obana et al. | |
| 2006/0184226 A1 | 8/2006 | Austin | |
| 2006/0184237 A1 | 8/2006 | Weber et al. | |
| 2007/0050006 A1 | 3/2007 | Lavelle | |
| 2007/0191927 A1 | 8/2007 | Bowe et al. | |
| 2007/0225659 A1 | 9/2007 | Melsheimer | |
| 2007/0282302 A1 | 12/2007 | Wachsman et al. | |
| 2007/0299499 A1 | 12/2007 | Hartley et al. | |
| 2008/0027528 A1 | 1/2008 | Jagger et al. | |
| 2008/0033354 A1 | 2/2008 | Hartley et al. | |
| 2008/0294230 A1 | 11/2008 | Parker | |
| 2009/0266238 A1 | 10/2009 | Mastropasqua et al. | |
| 2010/0057185 A1 | 3/2010 | Melsheimer et al. | |
| 2010/0160863 A1 | 6/2010 | Heuser | |
| 2010/0168674 A1 | 7/2010 | Shaw et al. | |
| 2010/0262157 A1 | 10/2010 | Silver et al. | |
| 2010/0268234 A1 | 10/2010 | Aho et al. | |
| 2011/0015728 A1 | 1/2011 | Jimenez et al. | |
| 2011/0121023 A1 | 5/2011 | Milan | |
| 2011/0178588 A1 | 7/2011 | Haselby | |
| 2011/0224742 A1 | 9/2011 | Weisel et al. | |
| 2012/0226341 A1 | 9/2012 | Schreck et al. | |
| 2013/0184805 A1 | 7/2013 | Sawada | |

OTHER PUBLICATIONS

European Office Action dated Jun. 28, 2011, from application No. 09774381.9.
European Office Action dated Jun. 30, 2014, from application No. 12178965.5.
European Office Action dated Mar. 9, 2016, from application No. 12178965.5.
Final Office Action dated Apr. 28, 2016, from U.S. Appl. No. 13/544,426.
Final Office Action dated Aug. 16, 2013, from U.S. Appl. No. 13/544,426.
Non-Final Office Action dated Apr. 29, 2019, from U.S. Appl. No. 15/639,028.
Non-final Office Action dated Feb. 26, 2013, from U.S. Appl. No. 13/544,426.
Non-final Office Action dated Jan. 27, 2014, from U.S. Appl. No. 13/544,426.
Non-final Office Action dated Oct. 13, 2011, from U.S. Appl. No. 12/496,446.
Non-final Office Action dated Sep. 11, 2015, from U.S. Appl. No. 13/544,426.
Non-final Office Action dated Sep. 26, 2016, from U.S. Appl. No. 13/544,426.
Notice of Allowance dated Aug. 19, 2019, from U.S. Appl. No. 15/639,028.
Notice of Allowance dated Feb. 13, 2017, from U.S. Appl. No. 13/544,426.
Notice of Allowance dated Mar. 7, 2012, from U.S. Appl. No. 12/496,446.
Notice of Allowance dated May 17, 2017, from U.S. Appl. No. 13/544,426.
Notice of Reasons for Refusal dated Jul. 10, 2012, from Japanese application No. 2011-516829.

* cited by examiner

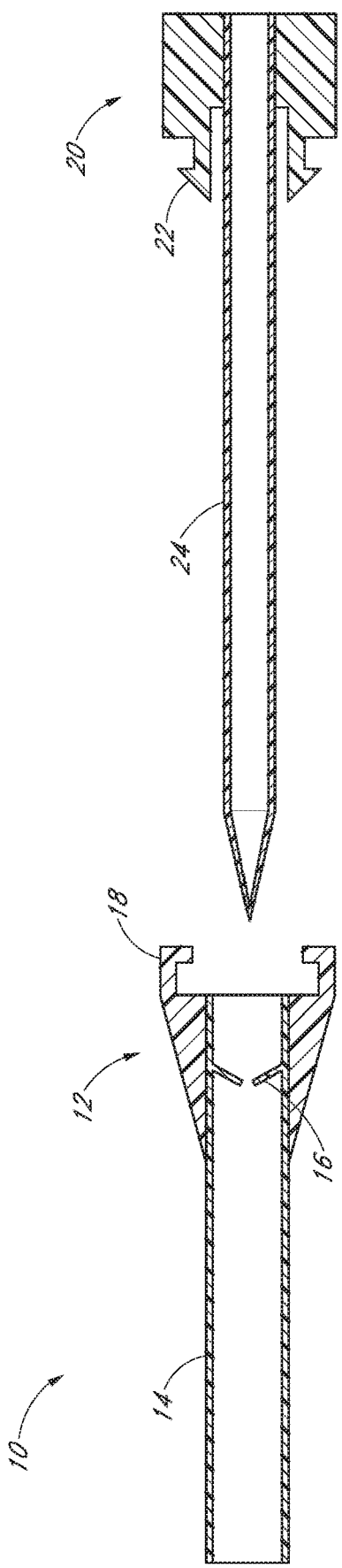
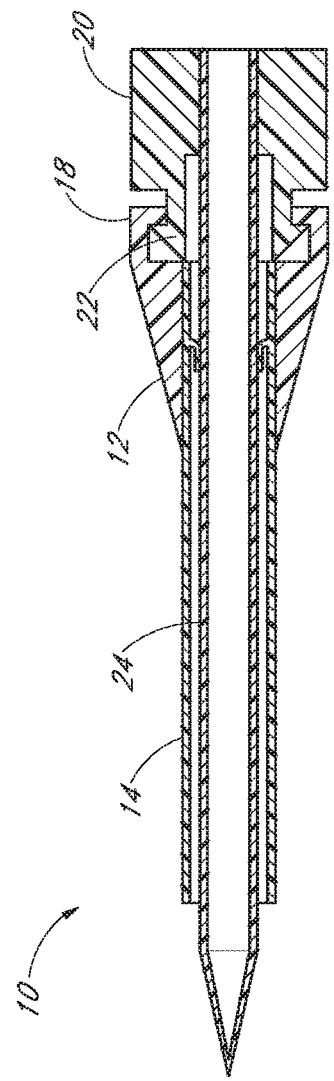
FIG. 1A
FIG. 1B

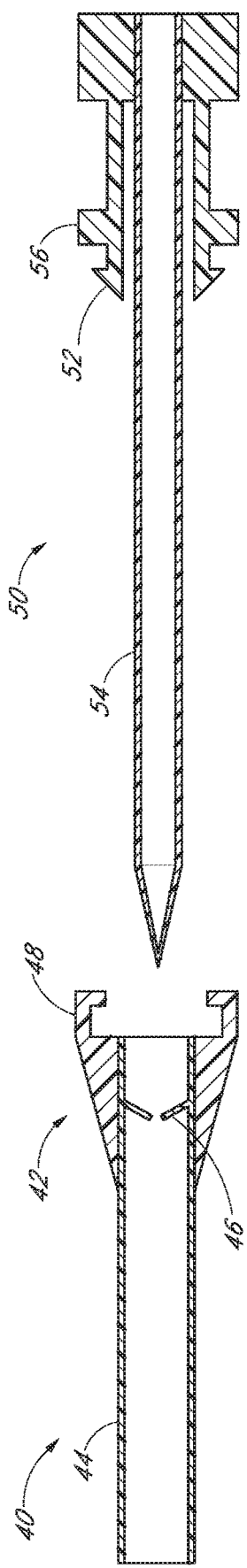
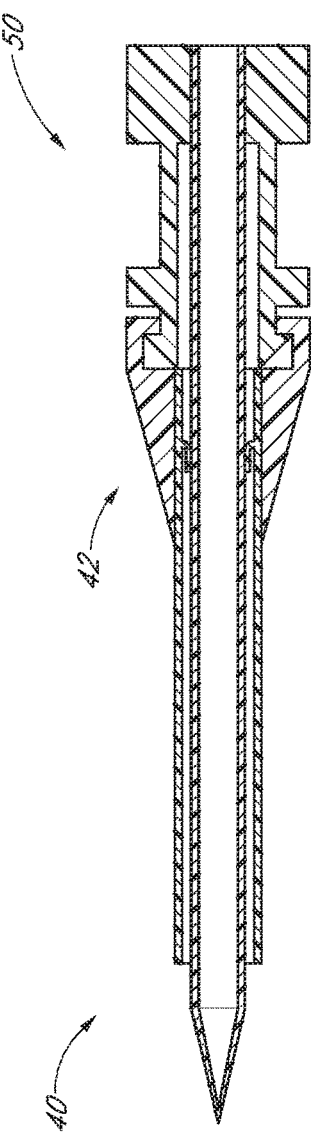
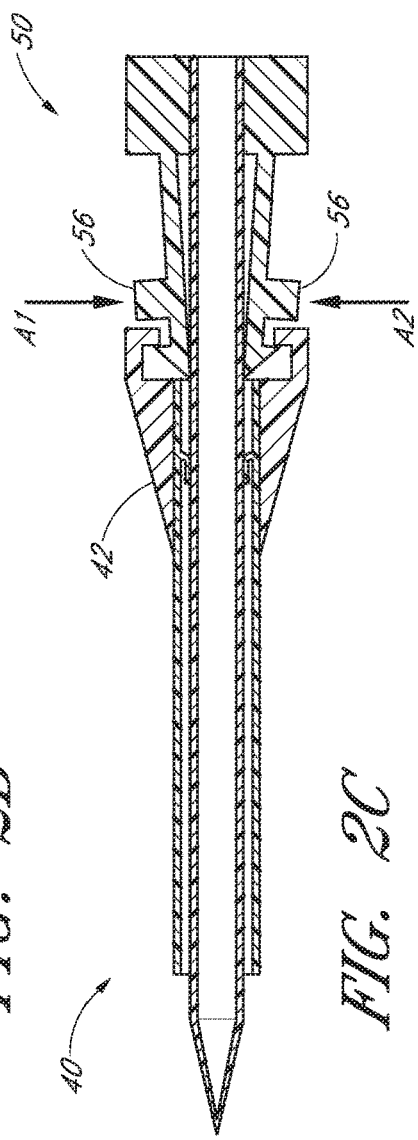
FIG. 2A
FIG. 2B
FIG. 2C

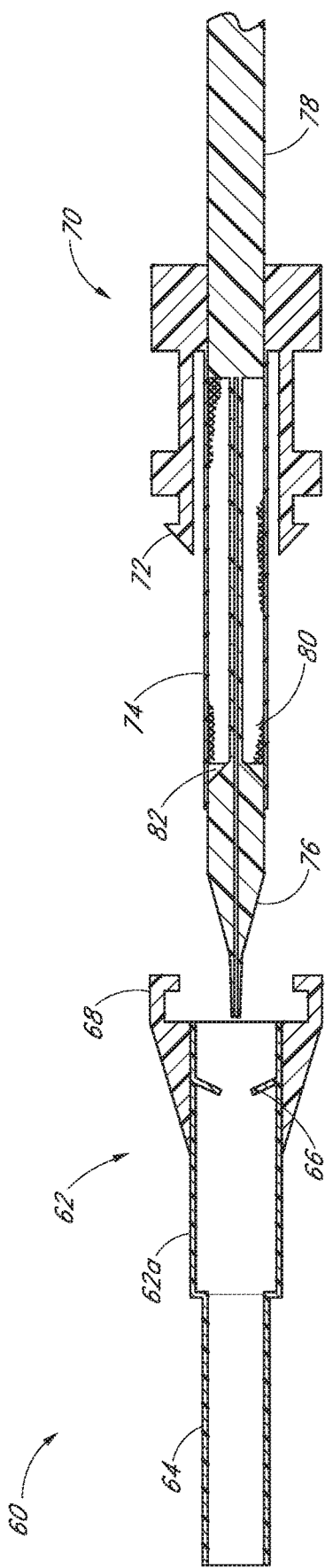
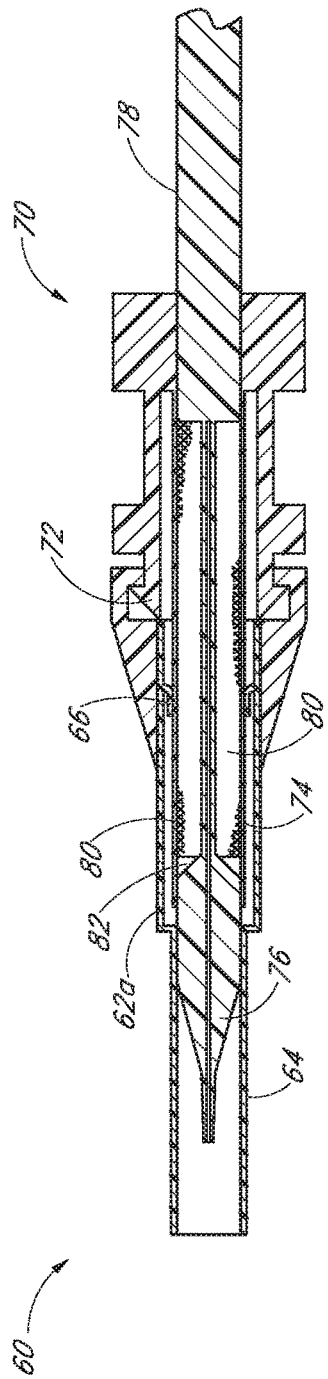
FIG. 3A
FIG. 3B

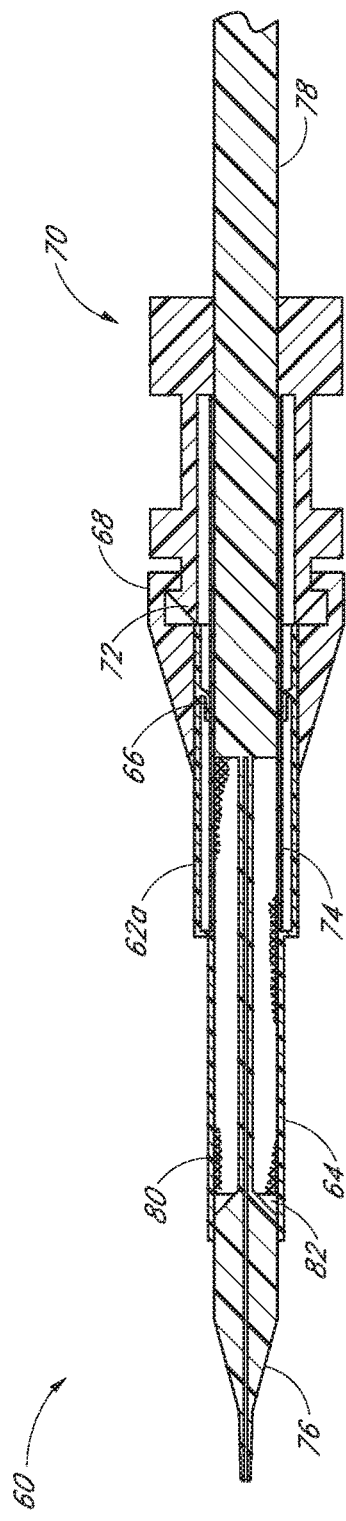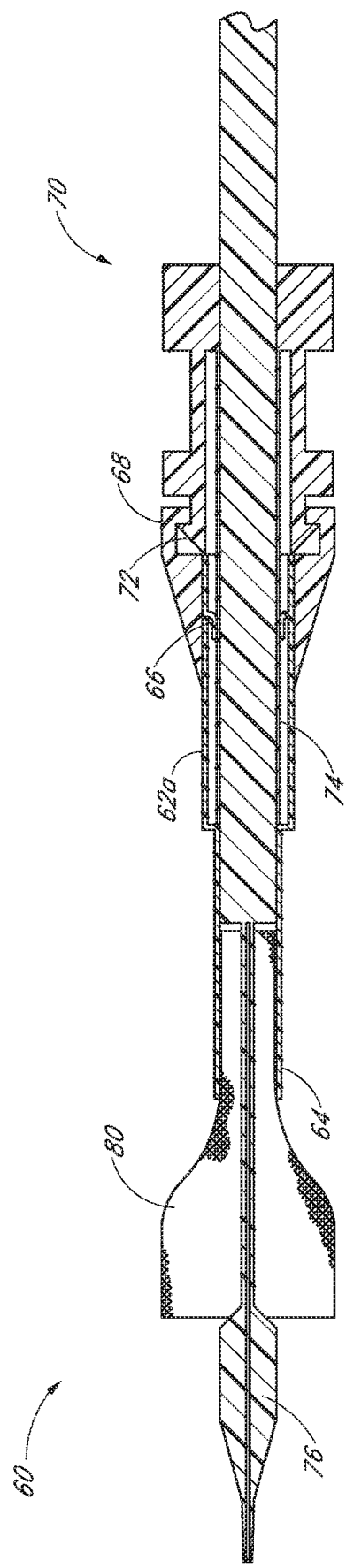

CATHETER SYSTEM AND METHODS OF USING SAME

PRIORITY CLAIM AND INCORPORATION BY REFERENCE

This application is a continuation of U.S. patent application Ser. No. 15/639,028, filed on Jun. 30, 2017, which is a continuation of U.S. patent application Ser. No. 13/544,426, now U.S. Pat. No. 9,700,701, filed on Jul. 9, 2012, which is a continuation of U.S. patent application Ser. No. 12/496,446, now U.S. Pat. No. 8,216,295, filed on Jul. 1, 2009 (entitled "CATHETER SYSTEM AND METHODS OF USING SAME"), which claims the benefit under 35 U.S.C. § 119 of U.S. Provisional Patent Application No. 61/077,429, filed Jul. 1, 2008 (entitled "CATHETER SYSTEM AND METHODS OF USING SAME"), and U.S. Provisional Patent Application No. 61/184,742, filed Jun. 5, 2009 (entitled "CATHETER SYSTEM AND METHODS OF USING SAME"), the entirety of each of which is hereby incorporated by reference as if fully set forth herein.

BACKGROUND OF THE INVENTION

Technical Field

The present invention relates to catheter systems, in particular, catheter systems having an introducer.

Description of the Related Art

Introducers or introducer sheaths are used for minimal invasive placement of catheters into blood vessels. They typically consist of a tubing that is inserted into the blood vessel and a seal or valve at the proximal end of the tubing which is positioned outside of the body. The seal provides a hemostasis seal against blood loss. Catheters used for diagnostic or therapeutic means are typically passed through the introducer into the blood vessel. The introducer sheath thus provides continuous access for catheters, protects the inner wall of the blood vessel against damage during catheter insertion, and provides a hemostasis seal against blood loss.

There are situations in which the catheters require substantial maneuvering within the blood vessel. For example, placement of a stent or stent graft may require the delivery catheter to be positioned precisely axially as well as possible rotationally into a specific location within the blood vessel. In addition deployment of the stent may require precise operation of the delivery system within the introducer. In these situations, the operator has to carefully control both the position of the introducer and the delivery system. This sometimes requires assistance by a second operator.

SUMMARY OF THE INVENTION

Some embodiments disclosed herein pertain to a catheter system for the insertion and positioning of diagnostic or therapeutic devices into blood vessels. In some embodiments, the system comprises an introducer or an introducer sheath and at least one catheter. The catheter can be introduced through the introducer into the blood stream. A docking mechanism can engage the proximal end of the introducer with the proximal end of the catheter and can prevent axial movement between the introducer and the catheter.

In some embodiments, a catheter system can comprise an introducer and a catheter, wherein the introducer can comprise a sheath (that can be tubular) and a seal that can be an adjustable hemostasis valve connected to the proximal of the sheath. The introducer can define a proximal end and a distal end, and the catheter can be configured to engage with the proximal end of the introducer. The introducer and the catheter can be configured such that the catheter can be slidingly received within the introducer. The introducer and the catheter can be configured such that the catheter can removably engage with the introducer such that, when the catheter is engaged with the introducer, the catheter will be axially fixed to the introducer so as to prevent substantial axial movement between the introducer and the catheter and so that the catheter and introducer can be manipulated in an axial direction as a single unit.

Additionally, in some embodiments, the catheter and introducer can be configured such that, when the catheter is engaged with the introducer, an inner core of the catheter can be rotatable relative to the introducer and the introducer sheath. Further, in some embodiments, the catheter can be configured such that the inner core of the catheter can be locked or substantially prevented from rotational movement relative to the outer sheath of the catheter and/or relative to the introducer.

In some embodiments, a method of placement of a catheter into a blood vessel is provided, wherein the catheter is passed through an introducer sheath and the proximal end of the introducer sheath physically engages with, or is removably docked with, the catheter to prevent substantial axial motion between the introducer sheath and the catheter.

Some stents or stent grafts (collectively referred to herein as a stent or stents) may require precise placement in both axial and circumferential direction. For example, stents or stent grafts with fenestrations require accurate placement of the fenestration at the branch vessel. The embodiments of the catheter systems disclosed herein can be configured to allow for the rotation of the delivery catheter and, hence, the stent, relative to the introducer sheath. In tight and calcified vessels there is often considerable friction between the outer sheath of the catheter and the vessel wall. In some of the embodiments disclosed herein, the delivery catheter and introducer can be configured such that the outer sheath of the delivery catheter will not be in direct contact with the vessel wall during the stent delivery procedure. Rather, in some embodiments, some or all of the length of the outer sheath of the delivery catheter can be contained within the introducer sheath, and the introducer sheath can be in direct contact with the vessel wall. This can considerably reduce the force required to rotate the delivery system relative to the patient's vessel. Accordingly, the delivery catheter and the introducer can be configured such that the delivery catheter can be substantially free to rotate within the introducer sheath.

In some embodiments, the friction that can otherwise impede the rotational freedom of the delivery catheter can be further reduced by lining the inner surface of the introducer sheath with a low-friction coating such as PTFE or applying hydrophilic coating to the outer surface of the delivery catheter or the inner surface of the introducer sheath.

Thus, in some embodiments, the introducer sheath can remain rotationally static or still while the deployment catheter is rotated within the introducer sheath. This can protect the delivery catheter and stent from being damaged, torqued, or stressed during the rotational manipulation of the delivery catheter and stent, and also prevent any damage or stress on the vessel wall from the rotation of the delivery catheter or stent.

Additionally, in some embodiments, delivery catheter can be configured to permit a user or medical practitioner to selectively control or prevent the rotational freedom of the delivery catheter and stent relative to the introducer, or the inner core of the delivery catheter and stent relative to the outer sheath of the delivery catheter. For example, in some embodiments, the delivery catheter can comprise a threaded hub supported at the proximal end portion of the delivery catheter configured to selectively constrict or tighten against an outer wall of the inner core of the delivery catheter. By constricting the hub against the inner core, the inner core can be prevented or inhibited from rotating relative to the introducer. By loosening the hub relative to the inner core, the rotational freedom of the inner core or delivery catheter relative to the introducer sheath can be restored.

In some embodiments, the hemostasis valve of the introducer sheath can be opened and closed by rotating the handle of the introducer sheath so as to be adjustable. Active adjustment of the hemostasis valve may be desired to seal against catheters with a wide range of diameters. The docking mechanism can allow the handle of the introducer sheath to be operated (i.e. rotated) while a catheter is inserted in and docked to the introducer sheath. Furthermore, the catheter can be rotationally locked by closing the valve.

Some embodiments are directed to a catheter system that can comprise an introducer comprising a main body, a introducer sheath projecting from the main body, and a first seal (which can be a rubber seal, an interference or close tolerance fit between adjacent components, an adjustable hemostasis valve, or any other suitable sealing component or feature) supported within the introducer, and a catheter comprising a main body, an outer sheath projecting from the main body, a second seal (which can be a rubber seal, an interference or close tolerance fit between adjacent components, an adjustable hemostasis valve, or any other suitable sealing component or feature) supported within the catheter, and an inner core that is advanceable through the main body, the second seal, and the outer sheath. The first seal can be configured to at least inhibit a flow of blood through the introducer when the catheter is engaged with the introducer. The second seal can be configured to at least inhibit a flow of blood through the catheter. The introducer sheath can be configured to axially receive at least the inner core therethrough. In some embodiments, the introducer can be configured to be selectively engageable with the catheter so that the catheter can be selectively and removably linked with the introducer in the axial direction such that, when the introducer and the catheter are linked, the axial movement of either of the introducer and the catheter will cause the simultaneous and equal axial movement of the other of the introducer and the catheter. In some embodiments, the catheter system can be configured such that, when the introducer and the catheter are linked, the catheter is rotatable relative to the introducer.

Some embodiments are directed to a catheter system that can comprise an introducer comprising a main body and an introducer sheath projecting from the main body, a catheter comprising a main body, an outer sheath projecting from the main body, and an inner core that is advanceable through the main body and the outer sheath. In some embodiments, the inner core can be configured to axially support a stent such that the stent can be advanced through the outer sheath by advancing the inner core through the outer sheath. The outer sheath can be configured to radially restrain the stent so that no additional radial restraint is required. In some embodiments, the outer sheath can be configured to radially restrain the stent in addition to other forms of restraint. The introducer sheath can be configured to axially receive at least the inner core therein. In some embodiments, the catheter system can be configured such that the outer sheath of the catheter does not advance into the introducer sheath when the catheter is fully axially advanced into the introducer. In some embodiments, the introducer sheath can be configured to directly radially restrain the stent while the stent is positioned within the introducer sheath.

Therefore, in some embodiments, the outer sheath of the catheter and the introducer sheath can be configured to provide a lumen having a generally uniform crosssectional size through the catheter system through which the endoluminal prosthesis can be advanced. In some embodiments, the lumen through the catheter system through which the endoluminal prosthesis can be advanced can be substantially continuous, so that the endoluminal prosthesis can be advanced through the catheter system without the prosthesis being obstructed by or snagging on any components or features of the catheter system as it is being advanced. In some embodiments, the lumen can be substantially continuous but have short gaps on the order of approximately 1 mm to approximately 3 mm in the lumen such as, without limitation, adjacent to the distal end of the outer sheath of the catheter and/or adjacent to the proximal end of the introducer sheath. Further, in some embodiments, one or more surfaces of other components comprising the catheter or the introducer in addition to the outer sheath and the introducer sheath, such as without limitation the main body of the introducer, can form portions of the lumen through the catheter system.

Some embodiments are directed to a method of deploying a stent in a blood vessel, comprising positioning an introducer within a patient's blood vessel so as to advance an introducer sheath of the introducer into the patient's blood vessel, the introducer having a proximal end portion and a distal end portion, advancing an outer sheath of a catheter into the introducer so that an end portion of the outer sheath of the catheter is positioned approximately adjacent to the proximal end portion of the introducer sheath and such that no portion of the outer sheath overlaps the introducer sheath, the catheter further comprising an inner core that is axially moveable within the outer sheath, axially supporting a stent with the inner core, axially advancing the inner core and the stent through the outer sheath of the catheter, through the introducer sheath, and past the distal end of the introducer sheath, and deploying the stent in the blood vessel.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 1A is a schematic representation of an embodiment of a catheter system comprising a docking arrangement to physically engage a catheter with an introducer sheath.

FIG. 1B is a schematic representation of the embodiment of the catheter system shown in FIG. 1A, showing the catheter engaged with the introducer sheath.

FIG. 2A is a schematic representation of another embodiment of a catheter system comprising a docking arrangement to physically engage a catheter with an introducer sheath.

FIG. 2B is a schematic representation of the embodiment of the catheter system shown in FIG. 2A, showing the catheter engaged with the introducer sheath.

FIG. 2C is a schematic representation of the embodiment of the catheter system shown in FIG. 2A, showing a mechanism for disengaging the catheter from the introducer sheath.

FIG. 3A is a schematic representation of another embodiment of a catheter system comprising a docking arrangement to physically engage a catheter with an introducer sheath, the catheter system being configured to deliver a stent or stent graft into a blood vessel.

FIG. 3B is a schematic representation of the embodiment of the catheter system shown in FIG. 3A, showing the catheter engaged with the introducer sheath.

FIG. 3C is a schematic representation of the embodiment of the catheter system shown in FIG. 3A, illustrating the axial insertion of an embodiment of a stent into the tubular sheath of the embodiment of the introducer sheath shown in FIG. 3A.

FIG. 3D is a schematic representation of the embodiment of the catheter system shown in FIG. 3A, illustrating the embodiment of the stent being deployed after the tubular sheath of the embodiment of the introducer sheath shown in FIG. 3A has been retracted from the stent.

DETAILED DESCRIPTION OF THE PREFERRED EMBODIMENTS

Figure 4:
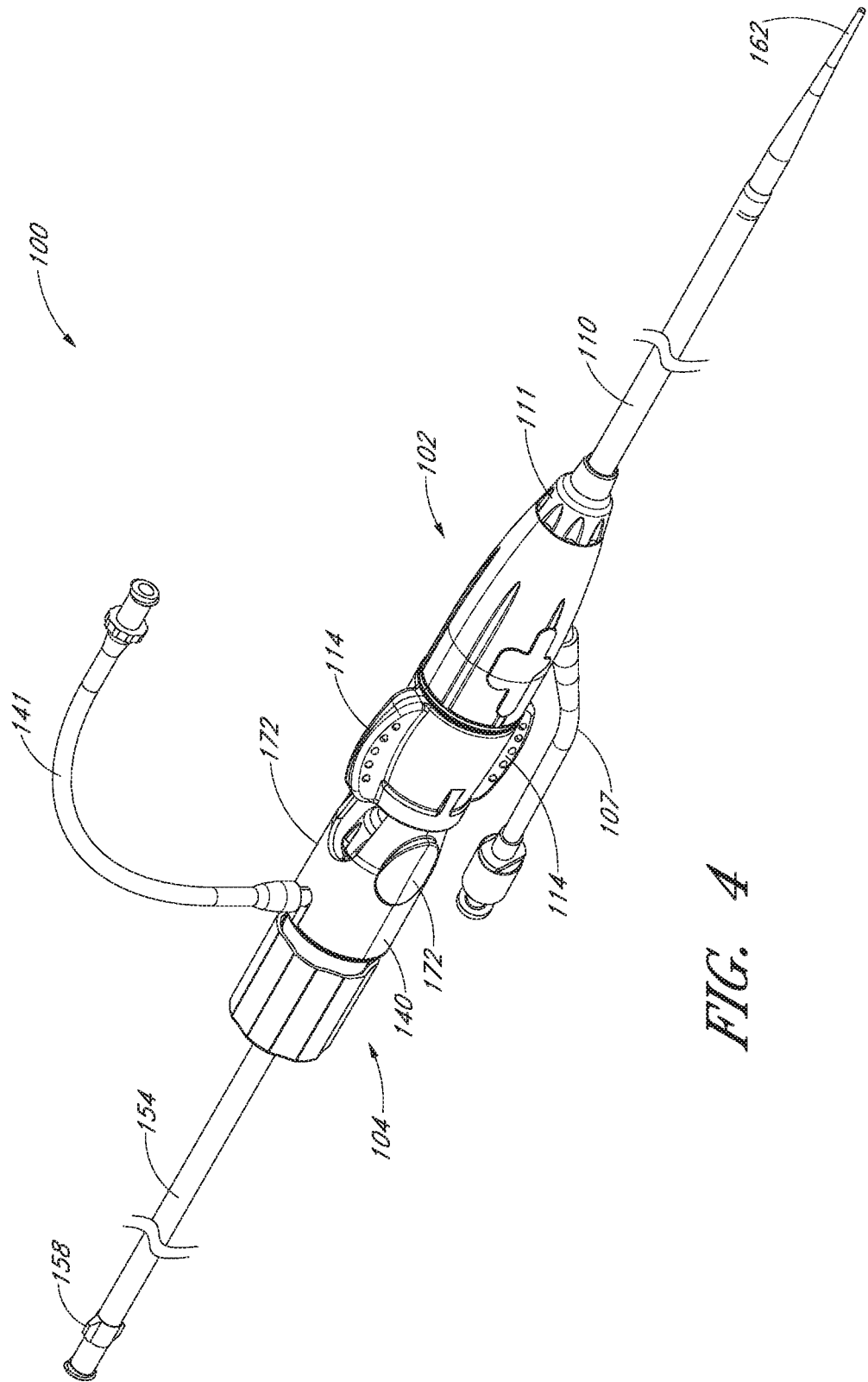
FIG. 4 is a perspective view of an embodiment of a catheter system comprising an embodiment of an introducer and an embodiment of a delivery catheter.

The following detailed description is now directed to certain specific embodiments of the disclosure. In this description, reference is made to the figures wherein like parts are designated with like numerals throughout the description and the drawings. Described below are various embodiments of a catheter system that can comprise an introducer sheath and a docking arrangement. In some embodiments, the catheter systems disclosed herein can be used in diagnostic or therapeutic procedures such as, but not limited to, endoluminal vascular prosthesis deployment procedures.

FIG. 1A is a schematic representation of an embodiment of a catheter system 10 comprising a docking arrangement configured to physically engage a catheter 20 with an introducer 12. FIG. 1B is a schematic representation of the catheter system 10 shown in FIG. 1A, showing the catheter 20 engaged with the introducer 12. In some embodiments, the catheter 20 or any catheter disclosed herein can be a diagnostic or therapeutic catheter, or any other suitable catheter. In some embodiments, the introducer 12 can comprise a tubular sheath 14, a seal 16, and a female docking mechanism 18. The first seal 16 can be a rubber seal, an interference or close tolerance fit between adjacent components, an adjustable hemostasis valve, or any other suitable sealing component or feature.

In some embodiments, the catheter 20 can have a shaft 24 and a male docking mechanism 22. In some embodiments, as illustrated in FIG. 1B, the catheter 20 can be inserted into the introducer 12 and the female docking mechanism 18 can be engaged with the male docking mechanism 22. In some embodiments, the docking mechanism can prevent the introducer 12 and the catheter 20 from moving axially with respect to each other when the docking mechanism is engaged. Additionally, in some embodiments, the catheter system 10 can be configured so that the catheter 20 can rotate within the introducer 12, even when the catheter 20 is docked with the introducer 12.

As mentioned, the introducer 12 can comprise a tubular introducer sheath 14 and a seal 16 (which, again, can be a rubber seal, an interference or close tolerance fit, an adjustable hemostasis valve, or any other suitable sealing component or feature) connected to the proximal end of the introducer sheath 14. In some embodiments, the overall design of the sheath 14 and seal 16 may be similar to the design of commercially available introducers, or any other introducers presently known or later developed. The catheter 20 can have an outside dimensional profile that is sized and/or configured to pass through the introducer sheath 14. As discussed above, in some embodiments, the proximal end of the catheter 20 and the proximal end of the introducer sheath 14 can be configured to permanently or removably engage with each other, and to allow for the rotation of the catheter 20 within the introducer sheath 14 while substantially limiting the axial movement of the catheter 20 with respect to the introducer sheath 14.

In some embodiments, after engagement of the catheter and introducer, the combined system can be operated by a single operator. As mentioned, the catheter system 10 can be configured so that the catheter 20 can substantially freely rotate within the introducer sheath 14, which can allow for precise rotational positioning of the catheter within the introducer. After completion of the procedure, the catheter 20 can be disengaged from the introducer 12 so that the catheter 20 can be removed from the patient's body. Additionally, the introducer 12 can be repositioned for a second intervention and a second catheter can be inserted and engaged with the introducer 12 for additional procedures.

FIG. 2A is a schematic representation of an embodiment of a catheter system 40 comprising a docking arrangement to physically engage a catheter 50 with an introducer 42. FIG. 2B is a schematic representation of the embodiment of the catheter system 40, showing the catheter 50 engaged with the introducer 42. FIG. 2C is a schematic representation of the embodiment of the catheter system 40 shown in FIG. 2A, showing a mechanism for disengaging the catheter 50 from the introducer 42.

In some embodiments, the catheter system 40 can have a male docking mechanism 52 and a shaft 54. The introducer 42 can comprise a tubular sheath 44, a seal 46, and a female docking mechanism 48. In particular, FIG. 2C schematically illustrates that the catheter 50 can be disengaged from the male docking mechanism 52 and the introducer 42 by compressing the levers or tabs 56. Accordingly, in the illustrated embodiment, the male docking mechanism 52 can be elongated and can comprise levers 56.

FIG. 3A is a schematic representation of another embodiment of a catheter system 60 comprising a docking arrangement to physically engage a catheter 70 with an introducer 62, the catheter system 60 being configured to deliver a stent or stent graft 80 into a blood vessel. FIG. 3B is a schematic representation of the embodiment of the catheter system 60 shown in FIG. 3A, showing the catheter 70 engaged with the introducer 62. FIG. 3C is a schematic representation of the embodiment of the catheter system 60 shown in FIG. 3A, illustrating the axial insertion of an embodiment of a stent or stent graft 80 into the tubular sheath 64 of the embodiment of the introducer 62 shown in FIG. 3A. FIG. 3D is a schematic representation of the embodiment of the catheter system 60 shown in FIG. 3A, illustrating the embodiment of the stent 80 being deployed after the tubular sheath 64 of the embodiment of the introducer 62 shown in FIG. 3A has been retracted from the stent 80.

Self-expanding stent or stents grafts are typically retained in a deployment sheath within the delivery catheter. The deployment sheath can protect the stent or stent graft and the vessel wall from damage during insertion and can retain the stent or stent graft in a collapsed low-profile configuration during delivery. The stent or stent graft can be deployed in the desired position of the blood vessel by removing the deployment sheath and allowing the stent or stent graft to radially expand against the wall of the blood vessel. In order to pass such a delivery catheter into the desired blood vessel, the catheter system can be configured so that the inner diameter of the introducer sheath is larger than the outer diameter of the deployment sheath. Clinicians prefer a low profile of the introducer sheath to minimize damage to the blood vessel and allowing for access into small blood vessels. It can be desired to minimize the profile of the delivery catheter.

Cartridge systems have been developed, in which the stent or stent graft can be transferred from delivery sheath into the introducer sheath and the stent or stent graft can be passed through the introducer sheath to the target location. In such a cartridge system, the introducer sheath effectively acts as a deployment sheath. The transfer eliminates the need of a second sheath and minimizes the profile of the system in the blood vessel. The docking arrangement of the current invention provides a secure engagement of the delivery catheter and the introducer sheath prior to transfer of the stent or stent graft into the introducer sheath. This prevents potential user errors in the transfer and further converts the delivery catheter and introducer sheath into a single-user system.

As illustrated in FIGS. 3A-3D, the catheter system 60 can be used to transfer and deploy a stent or stent graft 80 into a blood vessel (blood vessel not shown). As illustrated therein, the introducer 62 can comprise a tubular sheath 64 that can be inserted into the body of the patient. The proximal end 62*a* of the introducer 62 can be sized and/or configured to accommodate the deployment sheath 74 of the catheter 70. The introducer sheath can also have a seal 66 (referred to herein as a first seal) and a female docking mechanism 68, similar to any of the embodiments of the seal, hemostasis valve, and/or docking mechanisms described above. The seal 66 can be an annular rubber seal (as illustrated), an interference or close tolerance fit between adjacent components, an adjustable hemostasis valve, or any other suitable sealing component or feature. The stent delivery catheter 70 can comprise an inner core 78, a pocket 82 that can house the collapsed stent 80, a deployment sheath 74 that can retain the collapsed stent 80, and a catheter tip 76.

As illustrated in FIG. 3B, in some embodiments, the catheter 70 can be inserted into the introducer 62 when the docking mechanisms 68 and 72 are engaged. In some embodiments (not illustrated), the deployment sheath 74 of the delivery catheter 70 can be sized and configured to be received within the larger diameter proximal end 62*a* of the introducer sheath and to extend into the distal tubular sheath 64 of the introducer 62. Alternatively, in some embodiments, the deployment sheath 74 of the delivery catheter 70 can be sized and configured to be received within the larger diameter proximal end 62*a* of the introducer sheath but not the distal tubular sheath 64 of the introducer 62. In some embodiments, as illustrated in FIGS. 3C and 3D, the deployment sheath 74 and the tubular sheath 64 can be sized and configured such that, when the deployment sheath 74 has advanced through the proximal end 62*a* of the introducer sheath, the similar size or shape of the distal tubular sheath 64 can prevent the deployment sheath 74 from advancing through the distal tubular sheath 64. In some embodiments, the inner and/or outer diameters of the deployment sheath 74 and the tubular sheath 64 can be substantially the same.

As illustrated in FIG. 3C, in some embodiments, the inner core 78 of the catheter 70 can be pushed distally, thereby transferring the stent 80 from the deployment sheath 74 into the tubular sheath 64 of the introducer 62. The stent 80 can be advanced until the catheter tip 76 reaches the distal end of the tubular sheath 64. In this configuration, the catheter/introducer system effectively becomes a single-unit deployment catheter. Thus, in some embodiments, the tubular sheath 64 can function as a deployment sheath. In some embodiments, the stent 80 can be advanced in a collapsed configuration within the protective introducer 62 to the target location in the blood vessel without increasing the profile of the delivery system. If the delivery catheter were passed through a traditional introducer sheath, the sheath of the introducer would have to be of a larger diameter than the deployment sheath of the delivery catheter in order to accommodate the stent and the deployment sheath.

FIG. 4 is a perspective view of another embodiment of a catheter system 100 comprising an introducer catheter 102 (also referred to as an introducer) and a delivery catheter 104. The delivery catheter 104 can be configured for the delivery of an endoluminal prosthesis, or for any other suitable use. Therefore, the embodiments of the catheters and introducers disclosed herein can be configured for any suitable purpose, and the embodiments of the introducers disclosed herein can be configured to receive any suitable catheter design.

Figure 5:
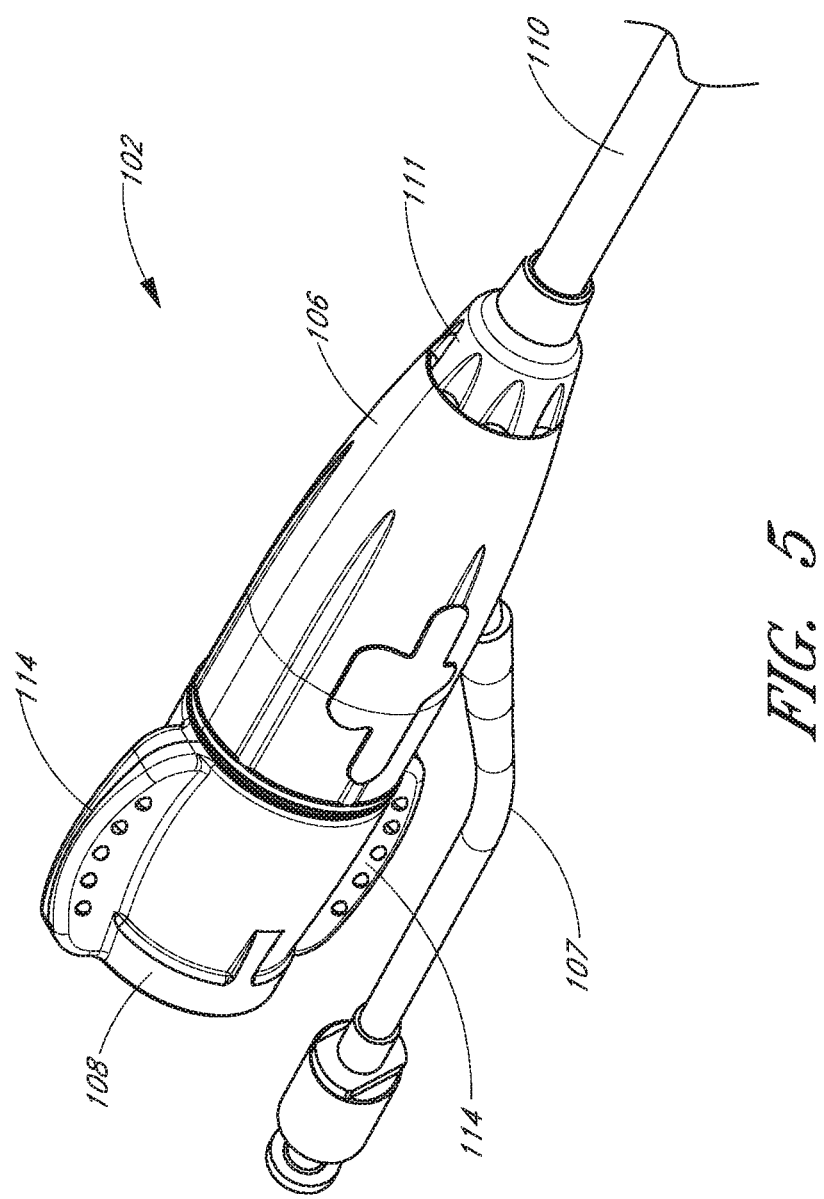
FIG. 5 is a perspective view of the embodiment of the introducer shown in FIG. 4.
Figure 6A:
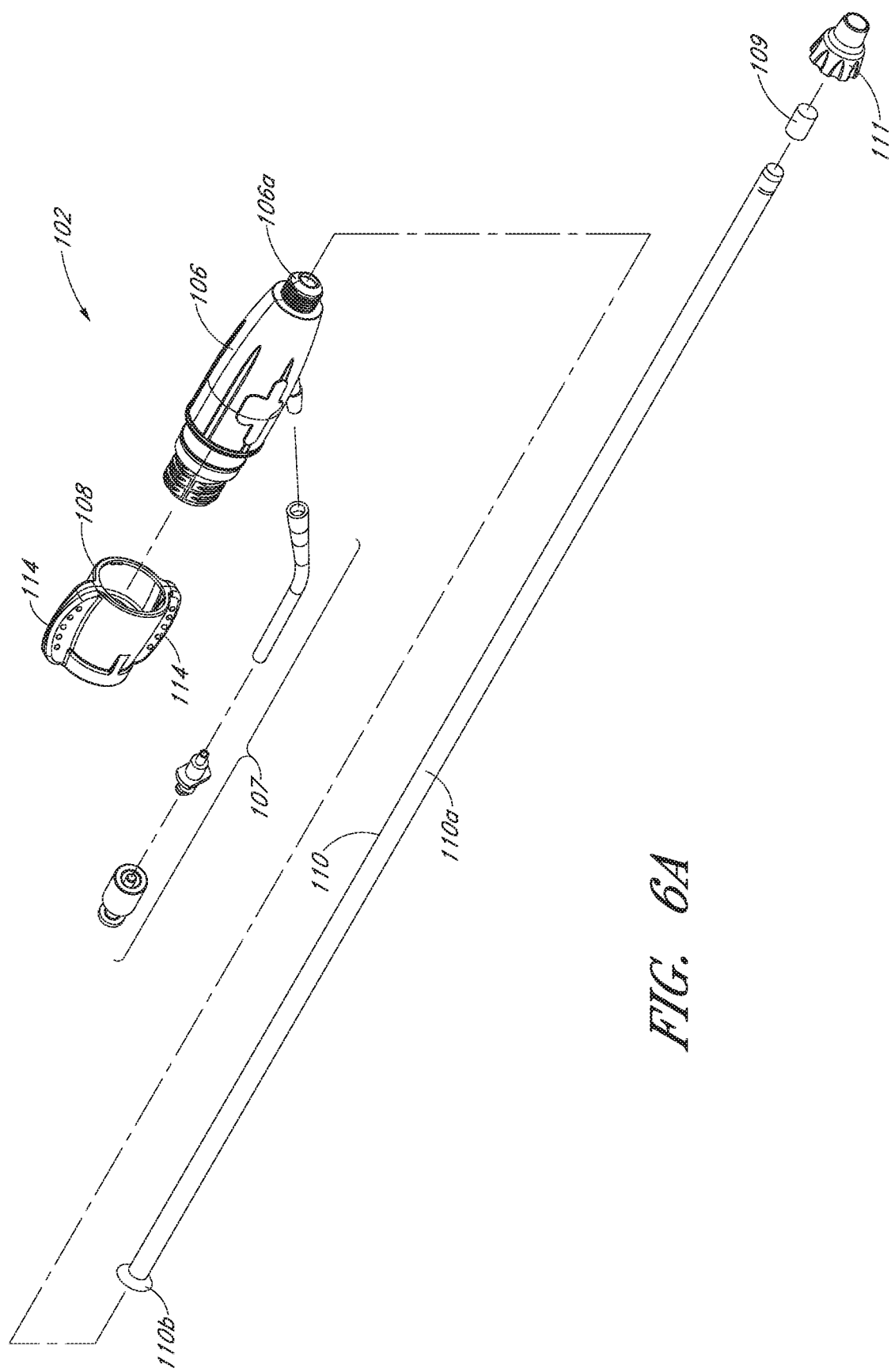
FIG. 6A is a first exploded assembly view of the embodiment of the introducer shown in FIG. 5.
Figure 6B:
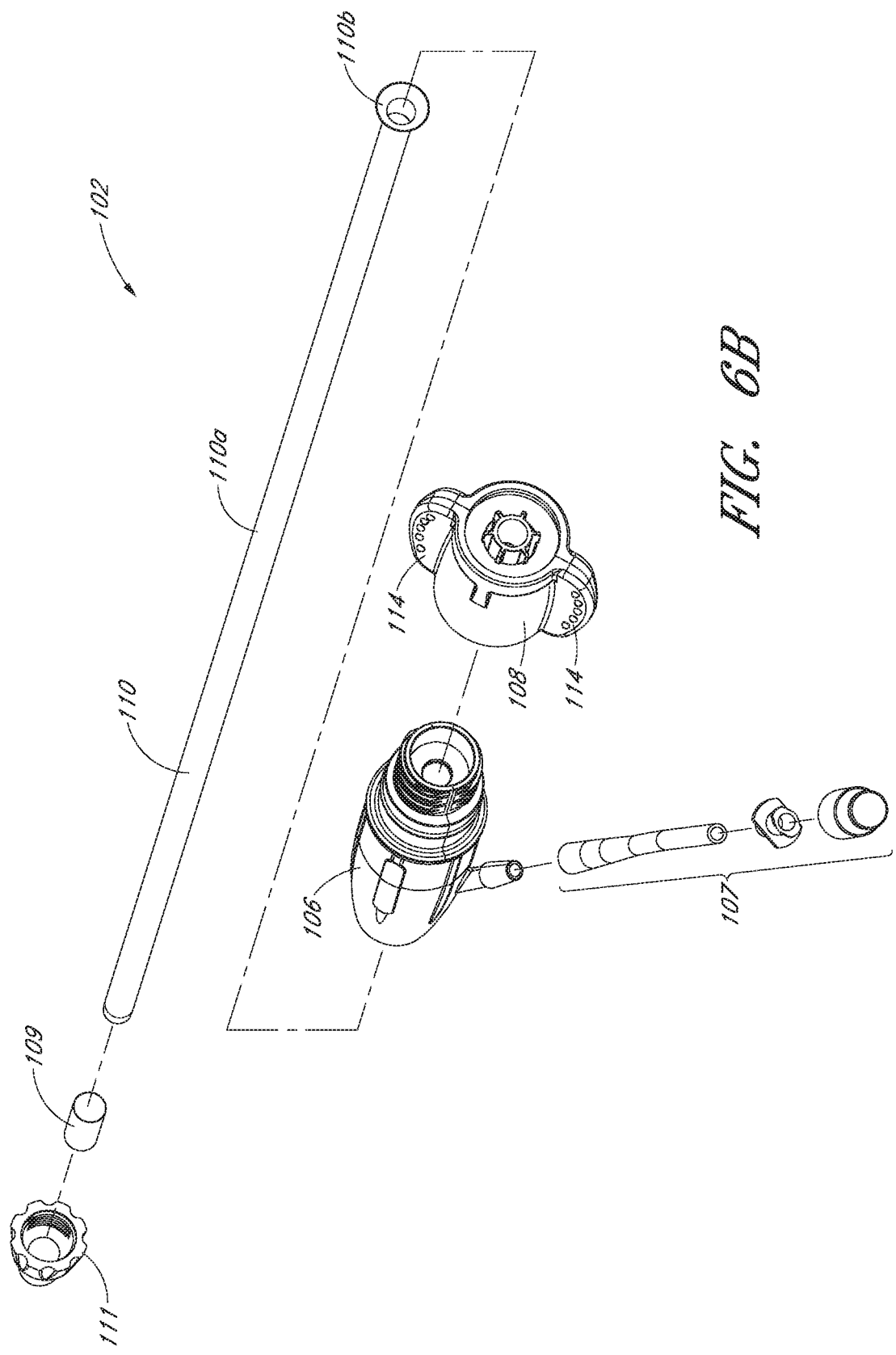
FIG. 6B is a second exploded assembly view of the embodiment of the introducer shown in FIG. 5.

FIG. 5 is a perspective view of the embodiment of the introducer 102 of the embodiment of the catheter system 100 shown in FIG. 4. FIGS. 6A and 6B are a first and a second exploded assembly view of the embodiment of the introducer 102 shown in FIG. 5. With reference to FIGS. 4-6, in some embodiments, the introducer 102 can have a main body 106, a threadably engageable hub portion 108, an introducer sheath 110, and a threaded cap 111 configured to threadably engage with a threaded end portion of the main body 106.

In some embodiments, a first tube 107 can be supported by the main body 106 so as to provide an orifice or access port into the main body 106. The first tube 107 can be used to flush the introducer 102 with saline or other suitable substances at any stage, such as but not limited to prior to the advancement of an endoluminal prosthesis through the introducer 102, or prior to other procedures for which an introducer may be used. The first tube 107 can support any suitable medical connector and/or valve on the distal end thereof.

The introducer sheath 110 can have an elongate portion 110a extending to any predetermined or desired length. As will be discussed in greater detail below, similar to the introducer 12 of the catheter system 10 described above, in some embodiments, the introducer sheath 110 can be configured such that an endoluminal prosthesis that is advanced into the introducer sheath 110 can be constrained or restrained by the introducer sheath 110. In this arrangement, the inside and/or outside diameter of the introducer sheath 110 can be approximately the same as or similar to the inside and/or outside diameter of the outer sheath of a delivery catheter that is engaged with the introducer 102. In some embodiments, the elongate portion 110a can be circular in cross-section (as illustrated), or can define any suitable crosssectional shape such as without limitation triangular, square, hexagonal, octagonal, or polygonal.

Further, as shown most clearly in FIG. 6A, the introducer sheath 110 can have a flared end portion 110b that can be configured to abut against a fore surface 106a of the main body 106. With reference to FIG. 6A, the elongate portion 110a of the introducer sheath 110 can pass through an opening formed in the cap 111 so that the flared portion 110b of the introducer sheath 110 can be engaged with and/or overlap an inside surface of the cap 111. In this configuration, the cap 111 supporting the introducer sheath 110 can be threadedly engaged with the main body 106 so that the introducer sheath 110 can be supported by the main body 106.

Additionally, with reference to FIGS. 6A and 6B, a tubular support or spacer 109 can be inserted over the elongate portion 110a of the introducer sheath 110 and positioned approximately adjacent to the flared portion 110b. The tubular spacer 109 can improve the fit and, hence, the seal between the outside surface of the introducer sheath 110 and the cap 111. The tubular spacer 109 can also provide additional support to the introducer sheath 110.

Figure 7:
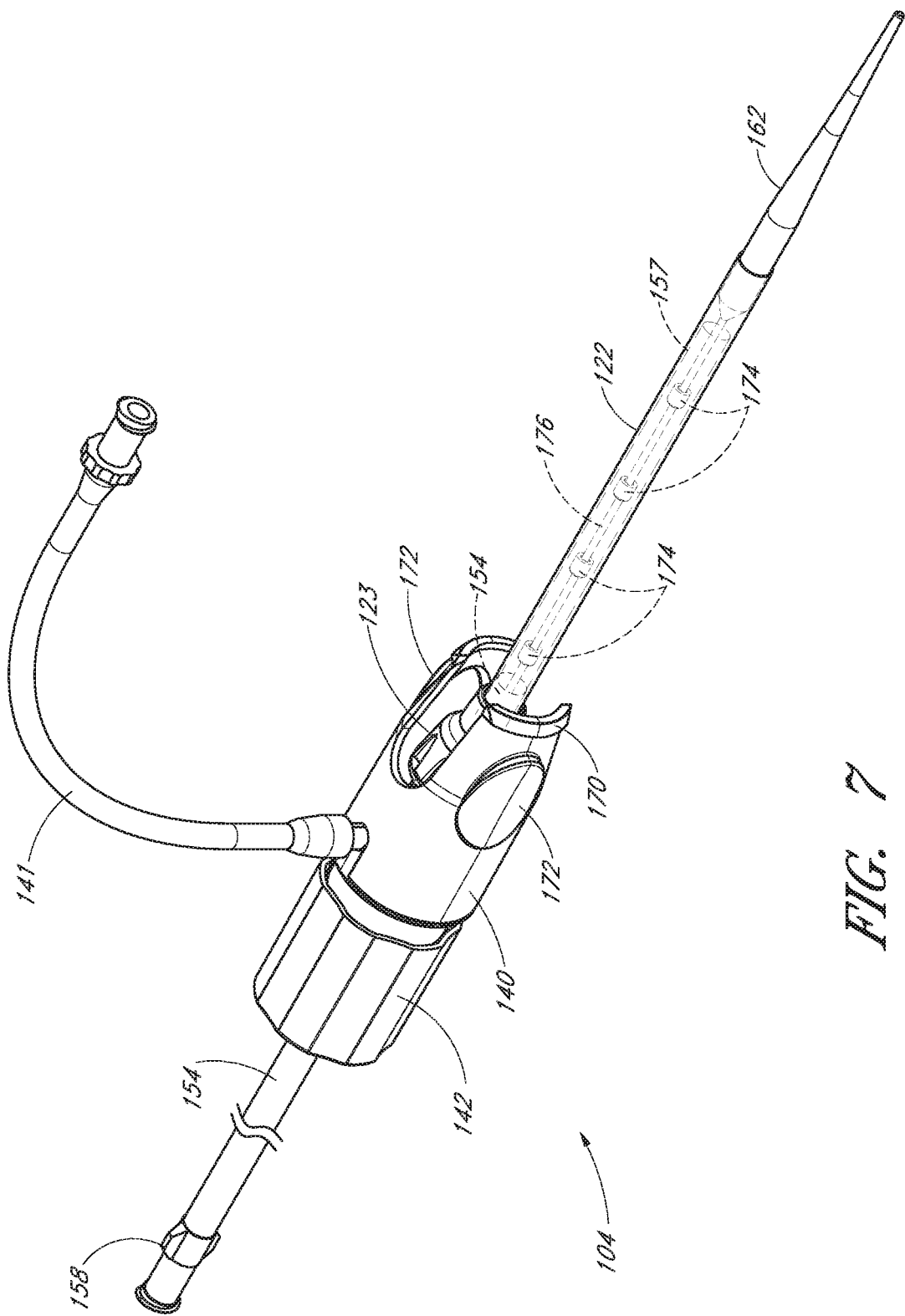
FIG. 7 is a perspective view of the embodiment of the delivery catheter shown in FIG. 4.
Figure 8A:
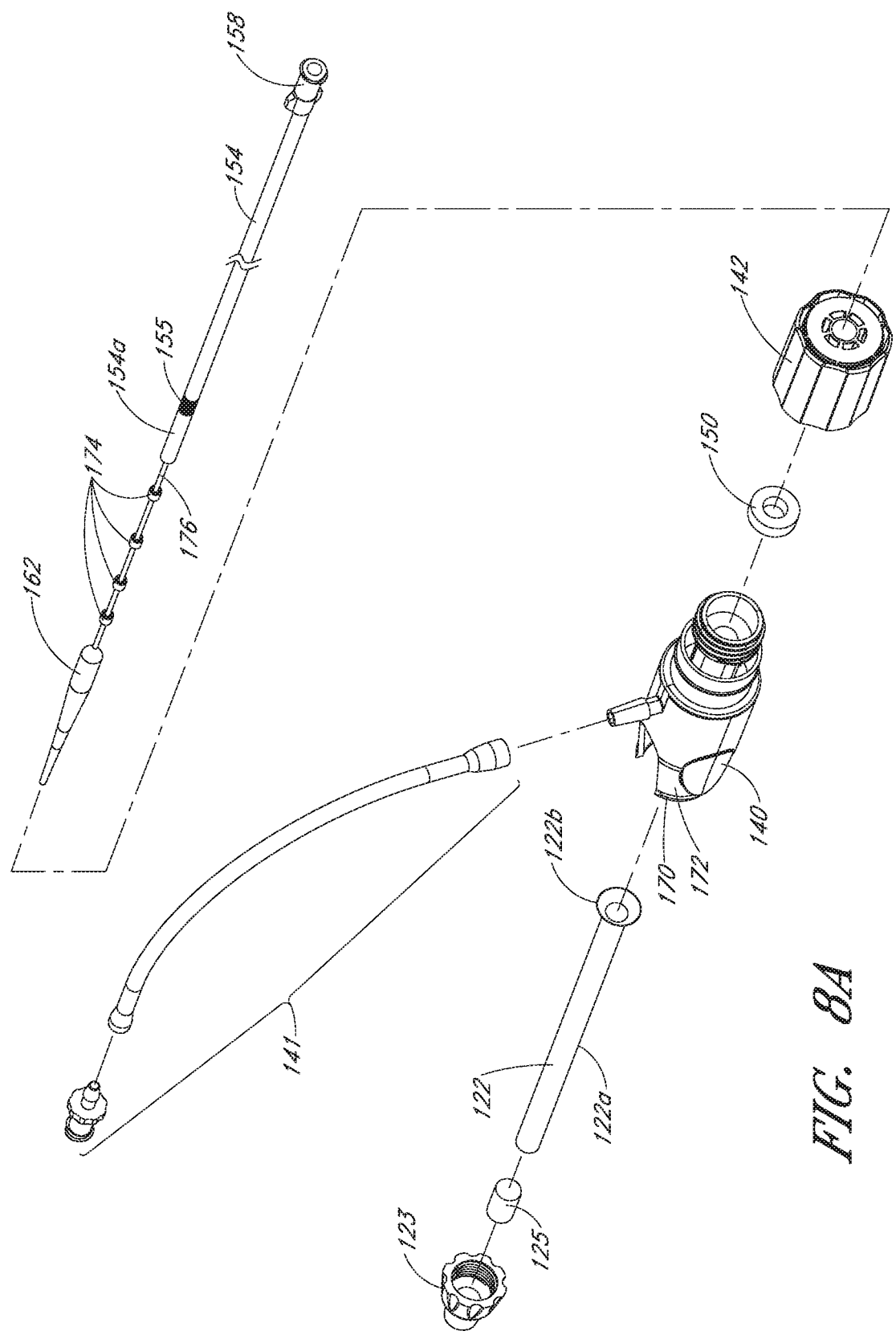
FIG. 8A is a first exploded assembly view of the embodiment of the delivery catheter shown in FIG. 7.
Figure 8B:
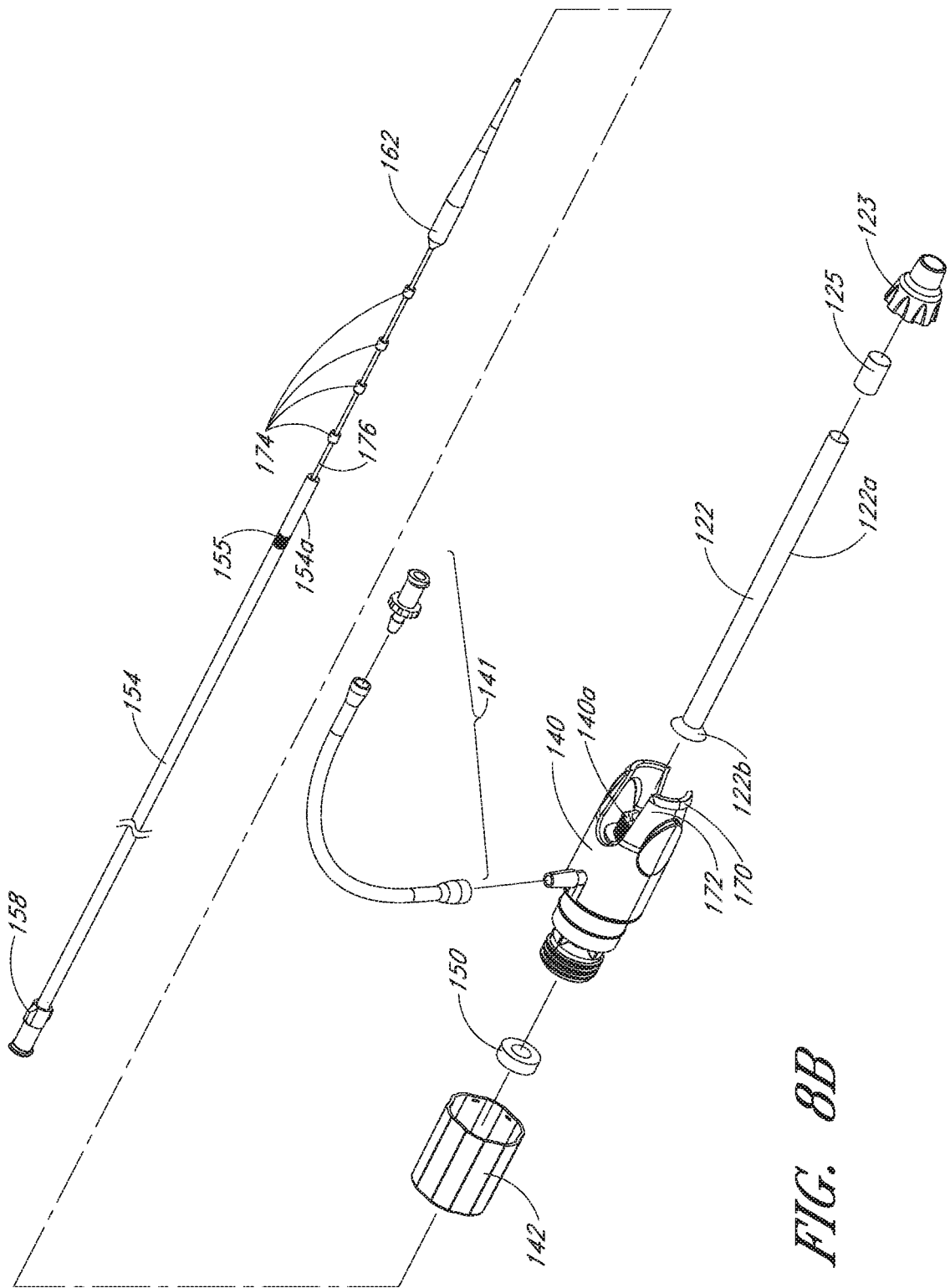
FIG. 8B is a second exploded assembly view of the embodiment of the delivery catheter shown in FIG. 7.
Figure 9:
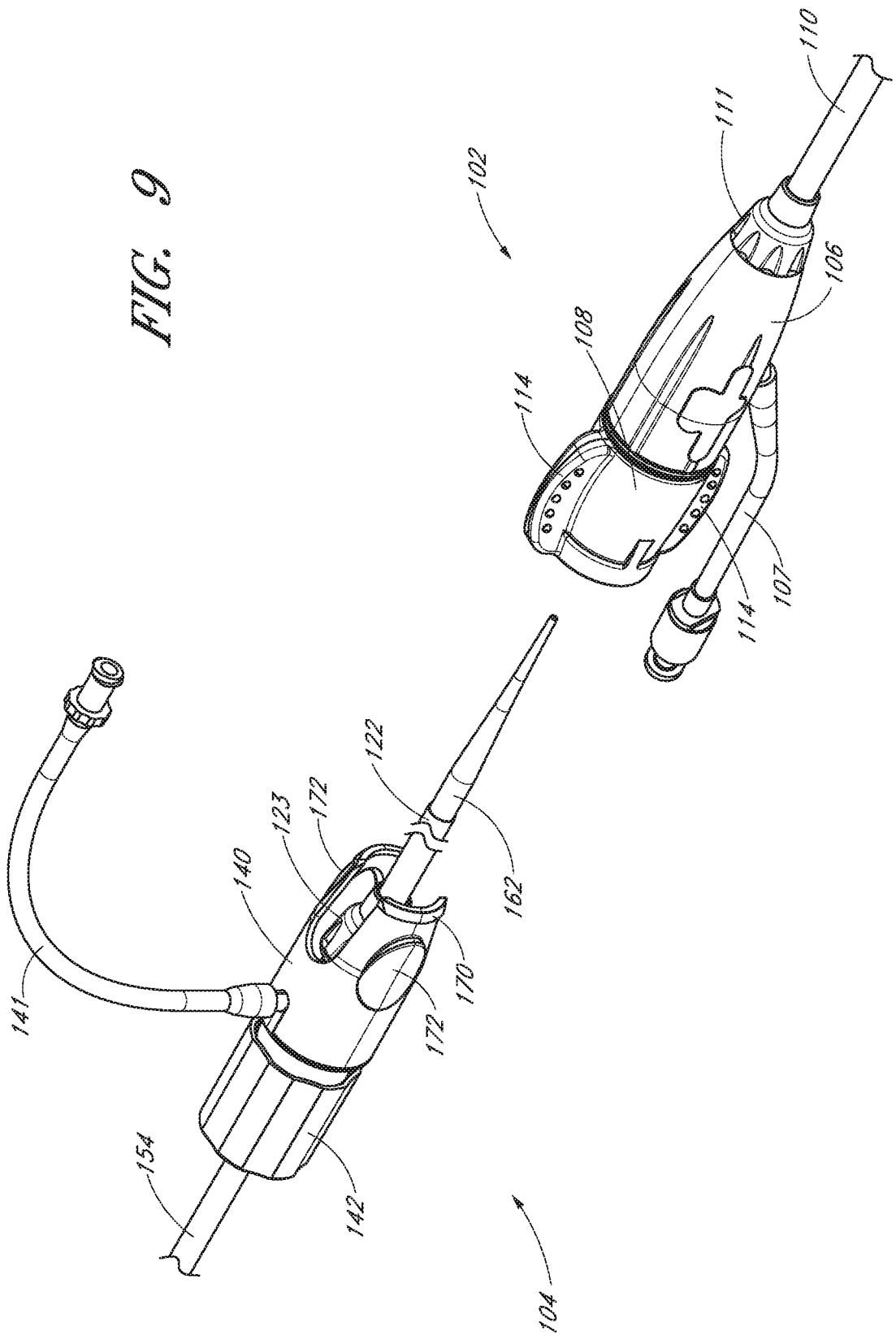
FIG. 9 is a perspective view of the embodiment of the catheter system shown in FIG. 4, showing the delivery catheter before the docking mechanism of the delivery catheter has been engaged with the docking mechanism of the introducer.
Figure 10:
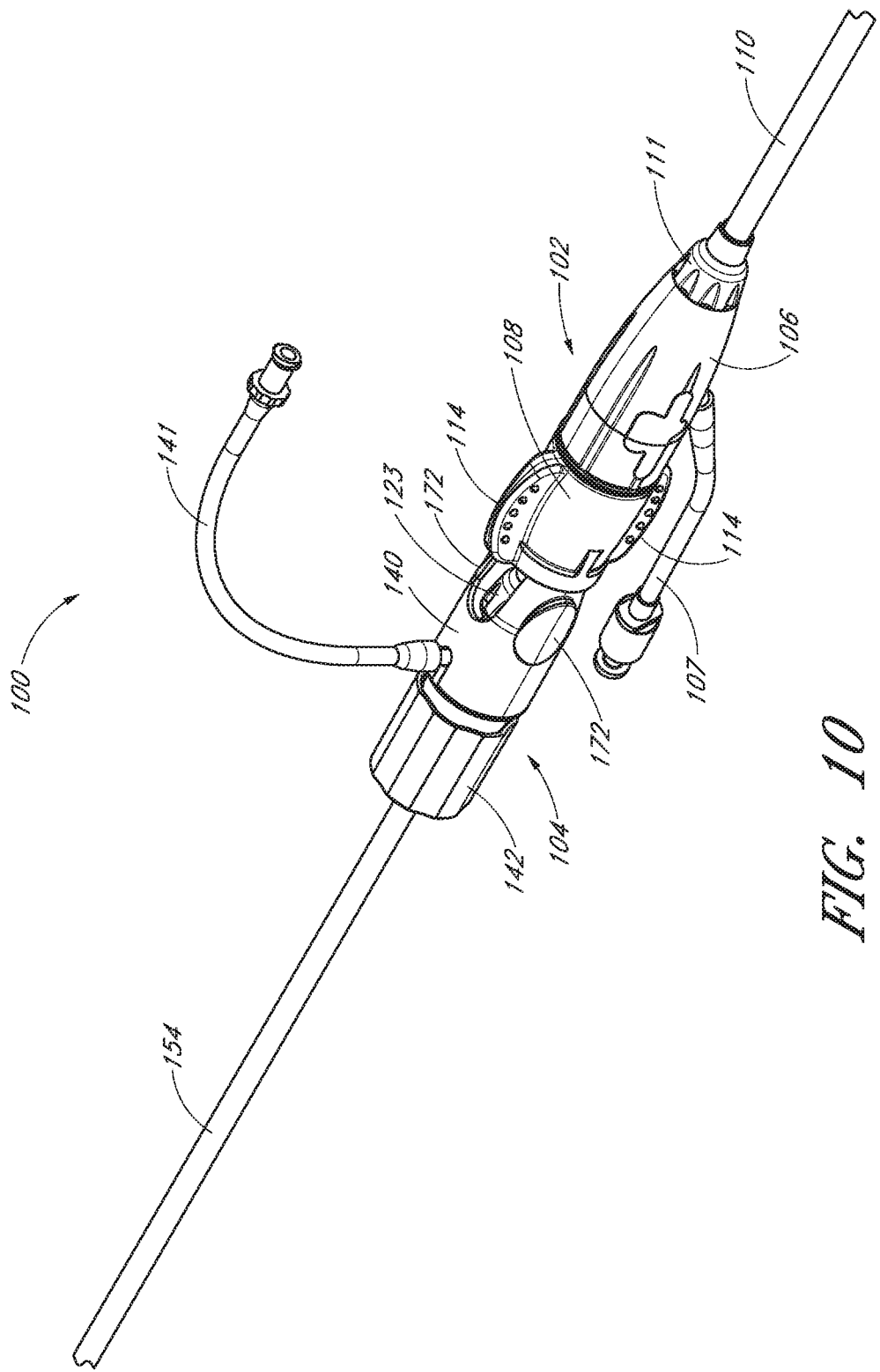
FIG. 10 is a perspective view of the embodiment of the catheter system shown in FIG. 4, showing the delivery catheter after the docking mechanism of the delivery catheter has been engaged with the docking mechanism of the introducer.

FIG. 7 is a perspective view of the embodiment of the delivery catheter 104 of the embodiment of the catheter system 100 shown in FIG. 4. FIGS. 8A and 8B are a first and second exploded assembly view of the embodiment of the delivery catheter 104 shown in FIG. 7. FIG. 9 is a perspective view of the embodiment of the catheter system 100 shown in FIG. 4, showing the delivery catheter 104 before the docking mechanism of the delivery catheter 104 has been engaged with the docking mechanism of introducer 102. FIG. 10 is a perspective view of the embodiment of the catheter system 100 shown in FIG. 4, showing the delivery catheter 104 after the docking mechanism of the delivery catheter 104 has been engaged with the docking mechanism of the introducer 102.

Figure 11:
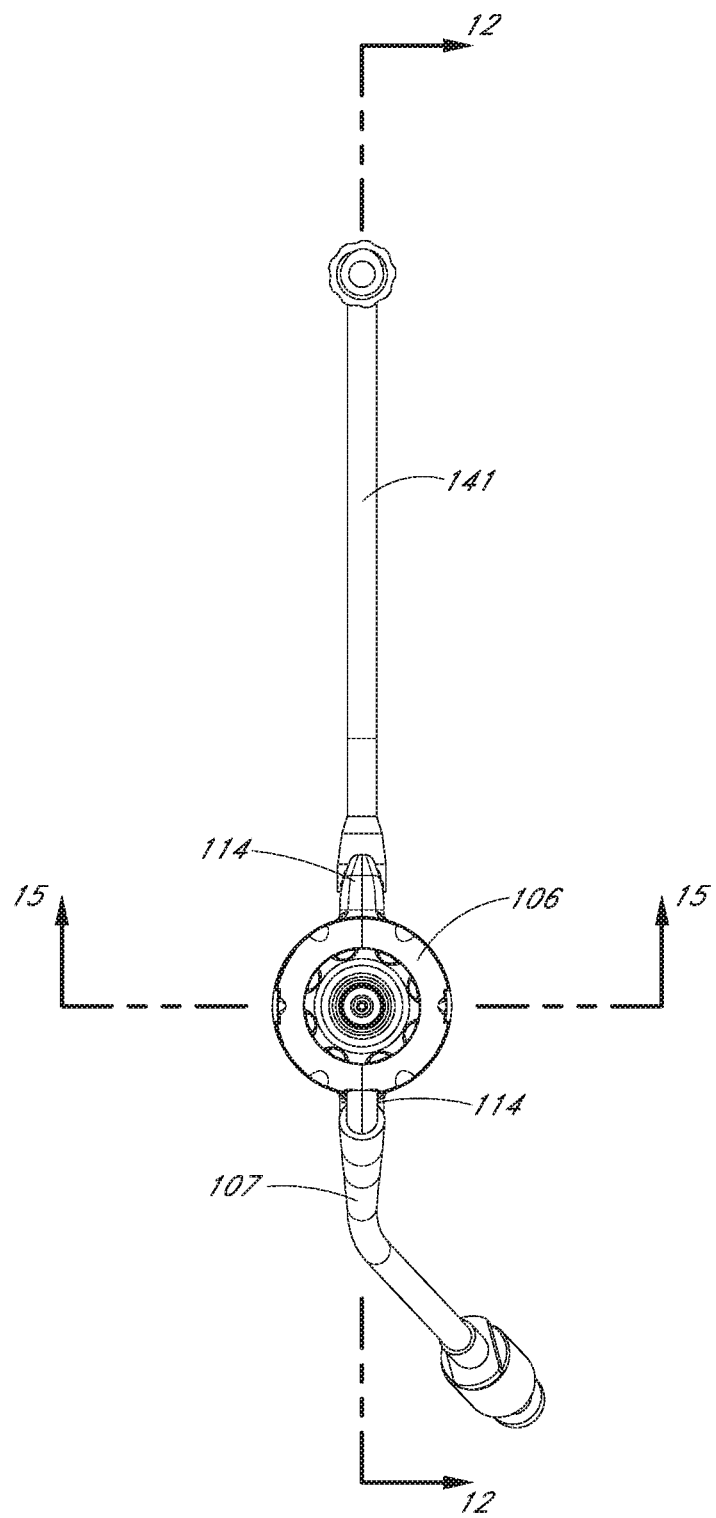
FIG. 11 is an end view of the embodiment of the catheter system shown in FIG. 4.
Figure 12:
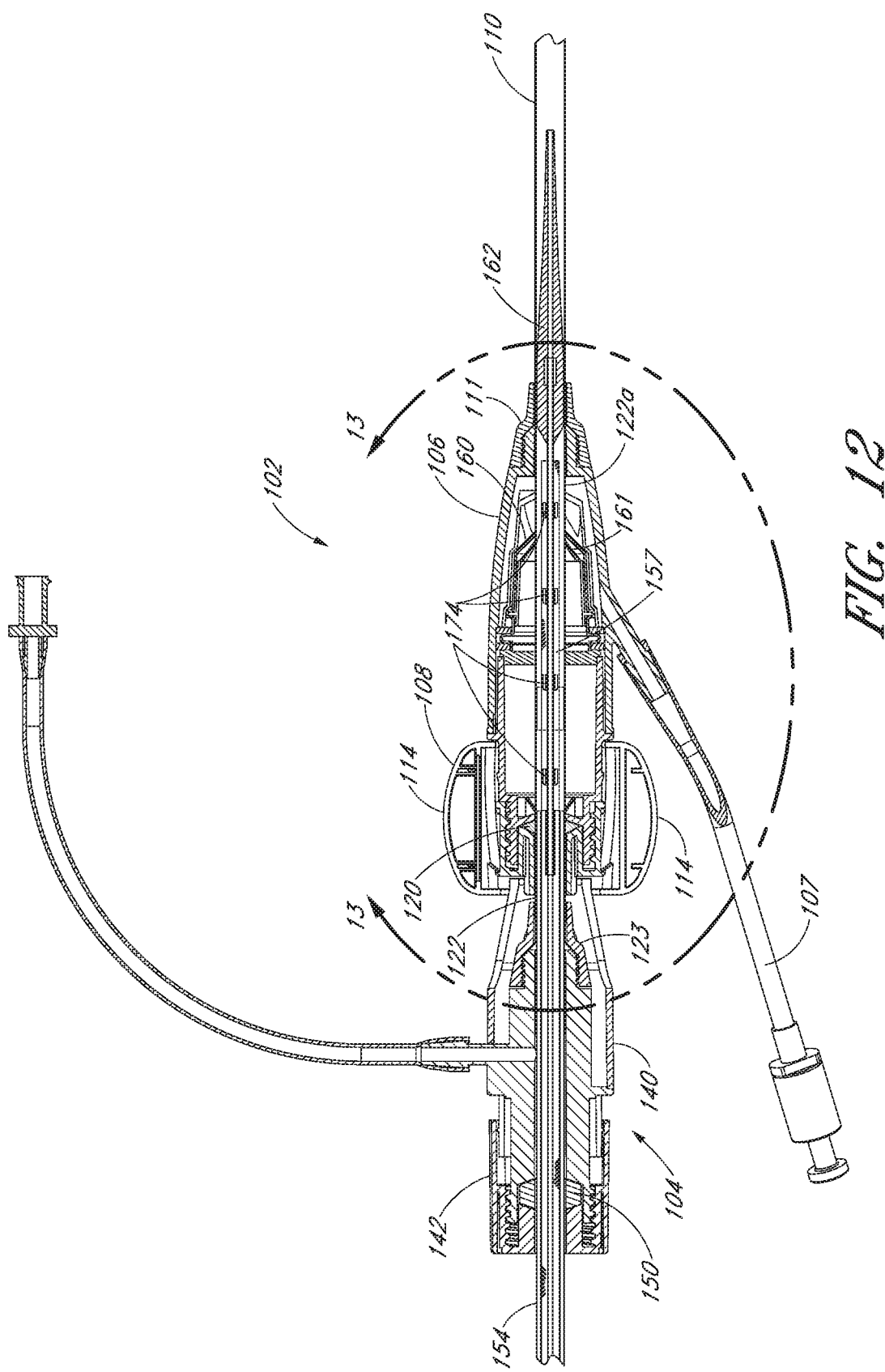
FIG. 12 is a section view of the embodiment of the catheter system shown in FIG. 4, taken through the line 12-12 of FIG. 11.
Figure 13:
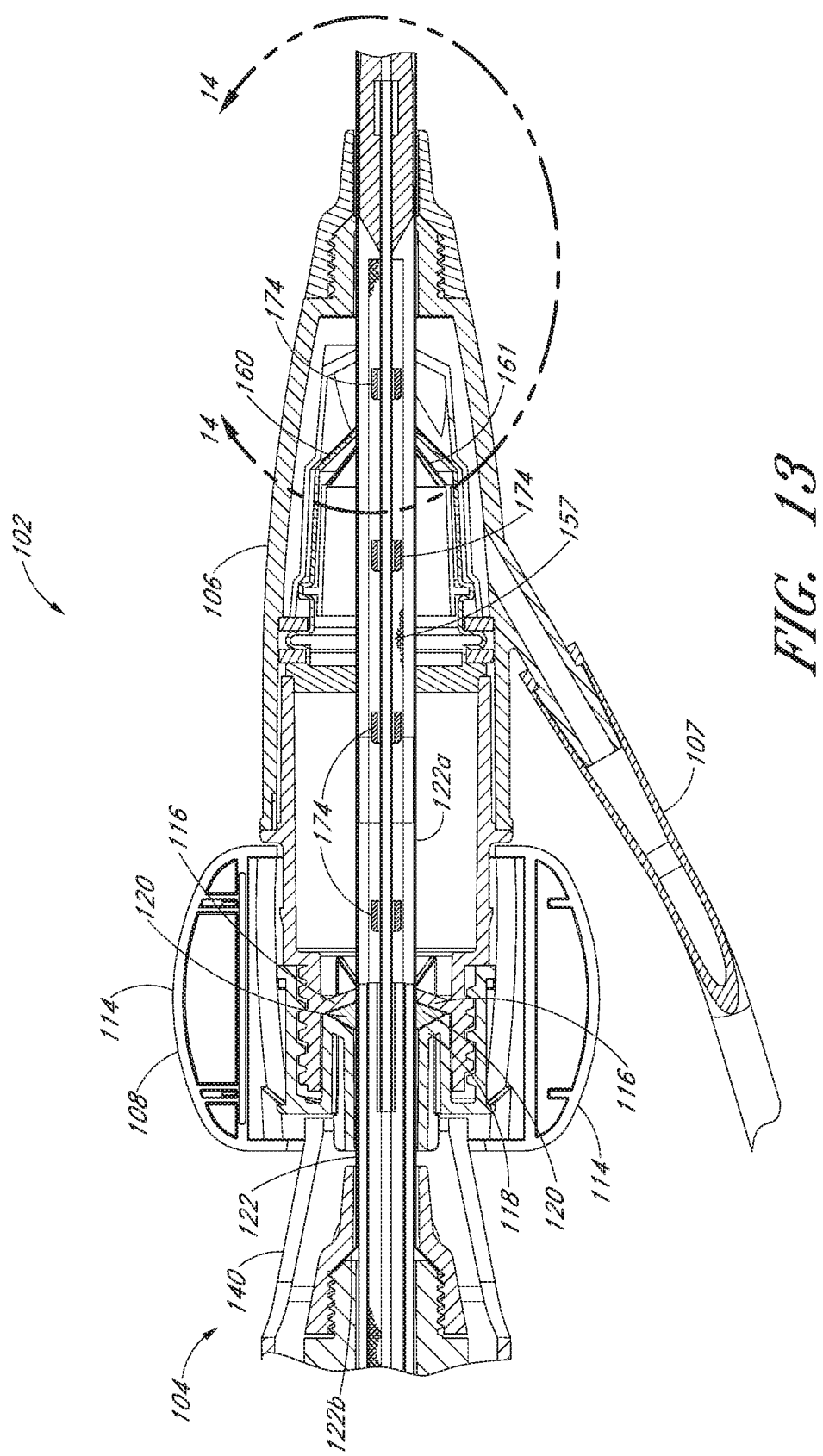
FIG. 13 is an enlarged section view of the embodiment of the catheter system shown in FIG. 4, defined by curve 13-13 of FIG. 12.
Figure 14:
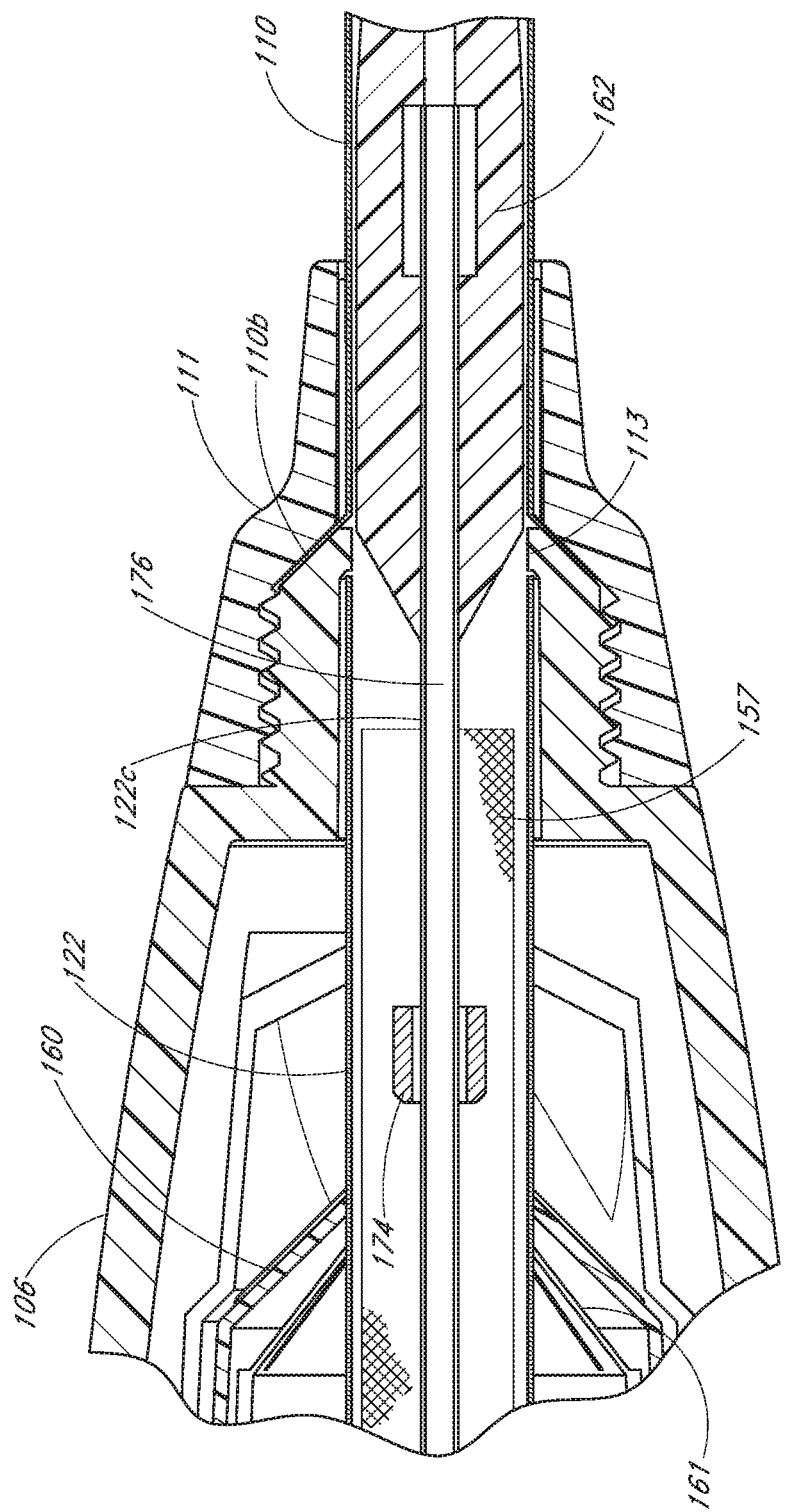
FIG. 14 is an enlarged section view of the embodiment of the catheter system shown in FIG. 4, defined by curve 14-14 of FIG. 13.

FIG. 11 is an end view of the embodiment of the catheter system shown in FIG. 4, with the delivery catheter 104 engaged with the introducer 102. FIG. 12 is a section view of the embodiment of the catheter system 100 shown in FIG. 4, taken through the line 12-12 of FIG. 11. FIG. 13 is an enlarged section view of the embodiment of the catheter system 100 shown in FIG. 4, defined by curve 13-13 of FIG. 12. FIG. 14 is an enlarged section view of the embodiment of the catheter system shown in FIG. 4, defined by curve 14-14 of FIG. 13. Finally, FIG. 15 is a section view of the embodiment of the catheter system shown in FIG. 4, taken through the line 15-15 of FIG. 11.

Figure 15:
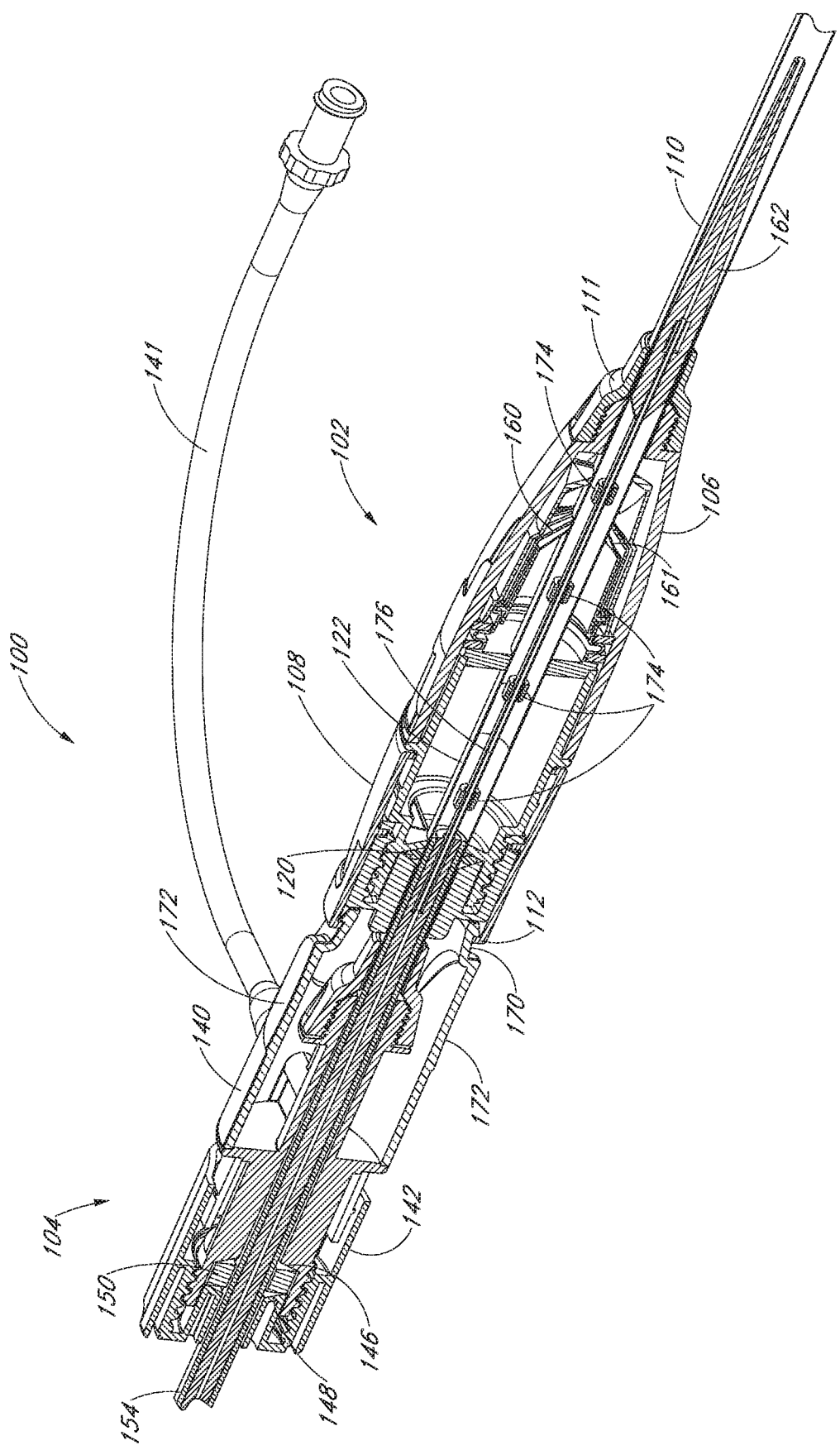
FIG. 15 is a section view of the embodiment of the catheter system shown in FIG. 4, taken through the line 15-15 of FIG. 11.

As shown most clearly in FIGS. 12 and 15, the hub portion 108 of the introducer 102 can have a docking mechanism or flange 112 or can be configured to removably receive or engage with the delivery catheter 104. In some embodiments, as in the illustrated embodiment, the docking mechanism 112 of the introducer 102 can be configured to be a female receiver, configured to receive a male docking member of the catheter 104, as will be described below. In some embodiments, the hub portion 108 can comprise one or more tabs 114 configured to improve a user's grip on the hub portion 108, and ability to rotate the hub portion 108 relative to the main body 106.

With reference to FIGS. 12, 13, and 15, some embodiments of the seal portion of the introducer 102 will be described. As mentioned above, the hub portion 108 can be configured to be threadably engageable with the main body 106. In some embodiments, the main body 108 can define an inner annular surface 116 that can be angled (so as to not be perpendicular to the axial centerline of the catheter system 100). In some embodiments, the surface 116 can be angled approximately 75 degrees relative to the axial centerline of the catheter system 100, or from approximately 65 degrees or less to approximately 80 degrees or more relative to the axial centerline of the catheter system 100. In some embodiments, the surface 116 can be approximately perpendicular to the axial centerline of the catheter system 100.

Similarly, in some embodiments, the hub portion 108 can define an inner annular surface 118 that can be angled so as to not be perpendicular to the axial centerline of the catheter system 100. In some embodiments, the surface 118 of the hub portion 108 can be angled approximately 75 degrees relative to the axial centerline of the catheter system 100, or from approximately 65 degrees or less to approximately 80 degrees or more and relative to the axial centerline of the catheter system 100 in a direction that is opposite to the direction of the angle defined by the surface 116 of the main body 106. In some embodiments, as in the illustrated embodiment, the shape and angular orientation of the surface 118 of the hub portion 108 can approximately mirror the shape and angular orientation of the surface 116 of the main body 106. In some embodiments, the surface 118 can be approximately perpendicular to the axial centerline of the catheter system 100.

An annular seal member 120 can be supported by the introducer 102 and positioned between the surface 116 of the main body 106 and the surface 118 of the hub portion 108. The seal member 120 can be formed from a resilient material, such as silicone, rubber or any other suitable material. The seal member 120 can be configured such that, when the hub portion 108 is threaded onto the main body 106, the surface 118 of the hub portion 108 can be moved axially toward the surface 116 of the main body 106, thereby compressing or squeezing the seal member 120. The relative angles of the surface 116 of the main body 106 and the surface 118 of the hub portion 108 can cause the seal member 120 to be forced against an outer sheath 122 of the delivery catheter 104 or other component of the delivery catheter 104 that is engaged with the introducer 102, thereby creating an adjustable seal between the outer sheath 122 of the delivery catheter 104, which can project distally from an end portion of the delivery catheter 104, and the introducer 102. In some embodiments, the level of seal can be adjusted by tightening or loosening the hub portion 108 of the introducer 102 relative to the main body 106 of the introducer 102. In some embodiments, the introducer 102 can be configured to provide a seal against devices with a profile ranging from 1 Fr to 20 Fr.

Alternatively, in some embodiments, any of the seals or seal portions described herein can be an interference or close tolerance fit between adjacent components such as, without limitation, the outer sheath 122 and one or more inside surfaces of the main body 106 or the hub portion 108 of the introducer 102. In some embodiments, any of the seals or seal portions described herein can be an interference or close tolerance fit between the inner core 154 and one or more inside surfaces of the main body 140 or the hub portion 142 of the catheter 104.

As shown in FIGS. 7, 8A, and 8B, some embodiments of the delivery catheter 104 can comprise a main body 140 and a hub portion 142 threadably engageable with the main body 140. Some embodiments of the delivery catheter 104 can also have an outer sheath 122 supported by the main body 140. In particular, the outer sheath 122 can be removably supported by the main body 140 using a cap 123 threadably supported by the main body 140. Further, in some embodiments, the outer sheath 122 can have an elongate portion 122a extending to any predetermined or desired length.

As mentioned above, in some embodiments, the inside and/or outside diameter of the outer sheath 122 of a delivery catheter 104 can be approximately the same as or similar to the inside and/or outside diameter of the introducer sheath 110. In some embodiments, the elongate portion 122a can be circular in cross-section (as illustrated), or can define any suitable crosssectional shape such as without limitation triangular, square, hexagonal, octagonal, or polygonal.

The outer sheath 122 can have a flared end portion 122b that can be configured to abut against a fore surface 140a of the main body 140. With reference to FIG. 8A, the elongate portion 122a of the outer sheath 122 can pass through an opening formed in the cap 123 so that the flared portion 122b of the outer sheath 122 can be engaged with and/or overlap an inside surface of the cap 123. In this configuration, the cap 123 supporting the outer sheath 122 can be threadedly engaged with the main body 140 as mentioned above so that the outer sheath 122 is supported by the main body 140.

Additionally, with reference to FIGS. 8A and 8B, a tubular support or spacer 125 can be inserted over the elongate portion 122a of the outer sheath 122 and positioned approximately adjacent to the flared portion 122b of the outer sheath 122. The tubular spacer 125 can improve the fit and, hence, the seal between the outside surface of the outer sheath 122 and the cap 123. The tubular spacer 125 can also provide additional support to the outer sheath 122.

Similar to the hub portion 108 of the introducer 102, the hub portion 142 of the delivery catheter 104 can be configured to be threadably engageable with the main body 140 of the delivery catheter 104. In some embodiments, the main body 140 can define an inner annular surface 146 that can be angled so as to not be perpendicular to the axial centerline of the catheter system 100. In some embodiments, the surface 146 can be angled approximately 75 degrees relative to the axial centerline of the catheter system 100, or from approximately 80 degrees or more to approximately 65 degrees or less relative to the axial centerline of the catheter system 100. In some embodiments, the surface 146 can be approximately perpendicular to the axial centerline of the catheter system 100.

In some embodiments, a second tube 141 can be supported by the main body 140 so as to provide an orifice or access port into the main body 140. The second tube 141 can be used to flush the delivery catheter 104 with saline or other suitable substances at any stage, such as but not limited to prior to the advancement of an endoluminal prosthesis through the delivery catheter 104 and/or introducer 102, or prior to other procedures for which an delivery catheter may be used. The second tube 141 can support any suitable medical connector and/or valve on the distal end thereof.

Similarly, in some embodiments, the hub portion 142 can define an inner annular surface 148 that can be angled so as to not be perpendicular to the axial centerline of the catheter system 100. In some embodiments, the surface 148 of the hub portion 142 can be angled approximately 75 degrees relative to the axial centerline of the catheter system 100, or from approximately 65 degrees or less to approximately 80 degrees or more relative to the axial centerline of the catheter system 100 in a direction that is opposite to the direction of the angle defined by the surface 146 of the main body 140. In some embodiments, the surface 148 can be approximately perpendicular to the axial centerline of the catheter system 100.

Similar to that of the introducer, in some embodiments, a seal or seal portion comprising an annular seal member 150 can be supported by the delivery catheter 104 and positioned between the surface 146 of the main body 140 and the surface 148 of the hub portion 142. The seal member 150 can be formed from a resilient material, such as silicone, rubber or any other suitable material. The seal member 150 can be configured such that, when the hub portion 142 is threaded onto the main body 140, the surface 148 of the hub portion 142 can be moved axially toward the surface 146 of the main body 140, thereby compressing or squeezing the seal member 150. The relative angles of the surface 146 of the main body 140 and the surface 148 of the hub portion 142 can cause the seal member 150 to be forced against the inner core 154 of the delivery catheter 104, thereby creating an adjustable seal between the inner core 154 the outer sheath 122 of the delivery catheter 104.

In some embodiments, the level of seal can be adjusted by tightening or loosening the hub portion 142 of the delivery catheter 104 relative to the main body 140 of the delivery catheter 104. Additionally, in some embodiments, the rotational freedom of inner core 154 of the delivery catheter 104 can be inhibited or prevented by tightening the seal member 150 as described above. Thus, the force exerted by the seal member 150 on the inner core 154 can be adjusted to permit the inner core 154 and/or other components to rotate relative to the main body 140 and hub portion 142 of the delivery catheter 104. As illustrated in FIG. 4, an end portion or cap 158 can be supported at the proximal end of the inner core 154 to facilitate a user's ability to axially slide and/or rotate that inner core 154 relative to the main body 140 and hub portion 142 of the delivery catheter 104. In some embodiments, the cap 158 can have wings or tabs formed thereon to increase the torque or rotational force that can be exerted on the inner core 154. Alternatively, in some embodiments, the seal or seal portion within the catheter 104 can be formed from an interference or close tolerance fit between adjacent components such as, without limitation, the inner core 154 and one or more inside surfaces of the main body 140 or the hub portion 142 of the catheter 104.

In some embodiments, the inner core 154 can have a band or other marking 155 near a distal end thereof. The marking 155 can be sized, positioned, and configured to provide a visual indication to the medical practitioner as to the location of the end portion 154*a* of the inner core 154 and/or the location of a catheter tip 162 as the inner core 154 is being advanced into or withdrawn from the introducer 102.

In some embodiments, as illustrated most clearly in FIGS. 12 and 13, an additional seal member 160 can be supported by the main body 106 of the introducer 102 to provide an additional seal between the outer sheath 122 of the delivery catheter 104 and the introducer 102. In some embodiments, the seal 160 can be a flap type seal formed from a conically shaped piece of resilient material such as, but not limited to, rubber having one or more slits therein to allow the distal tip 162 and the outer sheath 122 to pass therethrough. In some embodiments, a supported flange 161 can be supported within the main body 106 and positioned behind the seal 160 to support the seal 160 and maintain the position of the seal 160 so that the seal 160 does not become inverted when the delivery catheter 104 is removed from the introducer 102. In some embodiments, the distal tip 162 can be formed from a soft material such as rubber and can be configured to be atraumatic so as to prevent any damage to a patient's vasculature as the catheter 104 is being advanced through the patient's vasculature.

As mentioned above, in some embodiments, as in the illustrated embodiment, the docking mechanism 112 of the introducer 102 can be configured to receive a male docking member or portion of the catheter 104. In particular, with reference to FIGS. 7, 8A and 8B, one or more deflectable tabs 170 can be supported by the main body 140 of the catheter 104. In some embodiments, the tabs 170 can be deflected by pressing or exerting a radial inward force against pads 172, causing the ends of the tabs 170 to move radially inward toward the axial centerline of the main body 104. By deflecting the tabs 170 inwardly, the main body 140 of the catheter 104 can be moved axially into engagement with the hub portion 108 of the introducer 102. In some embodiments, the tabs 170 can be automatically deflected inwardly when the main body 140 of the catheter 104 is moved axially into engagement with the hub portion 108 of the introducer 102. Once the main body 140 of the catheter 104 is moved axially into engagement with the hub portion 108 of the introducer 102 so as to abut against the hub portion 108 of the introducer, the tabs 170 can be released, thereby removably locking the main body 140 of the catheter 104 to the hub portion 108 of the introducer 102.

In this configuration, the catheter 104 can be axially engaged with or locked to the introducer 102 so that a user can axially manipulate the introducer 102 and the catheter 104 simultaneously. Additionally, in some embodiments, in this configuration, as discussed above, the catheter system 100 can be configured such that at least the inner core 154 of the catheter 104 can be rotated relative to the main body 140 of the catheter 104 and the introducer 102.

In some embodiments, as shown in FIGS. 7, 8A, and 8B, the inner core 154 can have a central tube or wire 176 configured to support a stent, such as stent 157 illustrated in FIGS. 7 and 12-14. Additionally, one or more beads or tabs 174 can be formed on or supported by the central tube or wire 176. The tabs 174 can be configured to increase the axial support or connection between the inner core 154 and an endoluminal prosthesis supported by the central tube 176 when the prosthesis is supported in a collapsed configuration by the central tube 176. In some embodiments, the catheter 104 can be configured such that an opening passes through the distal tip 162, the central tube 176, and the inner core 124. The opening can be configured so that at least the distal tip 162, the central tube 176, and the inner core 124 can be advanced over a guidewire positioned within a patient's vasculature, such as is described in U.S. patent application Ser. No. 12/101,863 filed on Apr. 11, 2008 (titled: BIFURCATED GRAFT DEPLOYMENT SYSTEMS AND METHODS), which application is hereby incorporated by reference in its entirety as if fully set forth herein.

Additionally, in some embodiments (not illustrated), the tabs 174 can be sized, spaced, and otherwise configured to provide axially support to multiple individual stent segments. For example, without limitation, multiple independent or tethered stent segments can be positioned within a tubular or bifurcated graft, and the stent graft can be positioned relative to the tabs 174 such that the tabs 174 are positioned between the stent segments. This arrangement can reduce the overall diameter of the outer sheath 122, the introducer sheath 110, and other components comprising the catheter system, can enhance the axial support provided by the tabs 174 to the endoluminal prosthesis, and can allow for a more uniform distribution of support forces between the tabs 174 and the endoluminal prosthesis. In some embodiments, the tabs 174 can be sized, spaced, and otherwise configured so as to be positioned adjacent to the links, bends, loops, and/or other connectors formed in a tubular or bifurcated stent, such as the links, bends, loops, and/or other connectors comprising the embodiments of the stents disclosed in U.S. Pat. No. 6,077,296 titled ENDOLUMINAL VASCULAR PROSTHESIS, which patent is hereby incorporated by reference as if fully set forth herein.

With reference to FIGS. 13-15, the outer sheath 122 of the deployment catheter 104 can be advanced into an axial opening within the introducer 102 when the deployment catheter 104 is engaged with the introducer 102. In some embodiments, the outer sheath 122 can be sized and configured such that the distal end portion 122*c* of the outer sheath 122 can terminate within the introducer 102 prior or proximal to the proximal end or flared portion 110*b* of the introducer sheath 110. Although not required, the introducer 102 can have a constricted portion 113 formed in the main body 106 of the introducer. In some embodiments, as shown most clearly in FIG. 14, the catheter system 100 can be configured such that the distal end 122*c* of the outer sheath 122 terminates prior to or approximately adjacent to a constricted portion 113 of the main body 106 of the introducer 102.

In some embodiments (not illustrated), the distal end portion 122*c* of the outer sheath 122 can be positioned near to or approximately adjacent to the proximal end portion or the flared portion 110*b* of the introducer sheath 110, regardless of whether the catheter 104 has a constricted portion 113. The inner diameter of the constricted portion 113 can be approximately the same as the inner diameter of the outer sheath 122 and/or the inner diameter of the introducer sheath 110.

Therefore, in some embodiments, the outer sheath 122 of the catheter 104 and the introducer sheath 110 can be configured to provide a lumen having a generally uniform crosssectional size through the catheter system through which the endoluminal prosthesis can be advanced. In some embodiments, the lumen through the catheter system 100 through which the endoluminal prosthesis can be advanced can be substantially continuous, so that the endoluminal prosthesis can be advanced through the catheter system 100 without the prosthesis being obstructed by or snagging on any components or features of the catheter system 100 as it is being advanced. In some embodiments, the lumen can be substantially continuous but have short gaps on the order of approximately 1 mm to approximately 3 mm in the lumen such as, without limitation, adjacent to the distal end of the outer sheath 122 of the catheter 104 and/or adjacent to the proximal or flared end 110b of the introducer sheath 110. For example, in some embodiments, short gaps can be formed adjacent to the distal end of the outer sheath 122 of the catheter 104 and/or adjacent to the proximal or flared end 110b of the introducer sheath 110 as some components comprising the catheter system 100 are threadedly engaged with other components comprising the catheter system 100. Further, in some embodiments, one or more surfaces of other components comprising the catheter 104 or the introducer 102 in addition to the outer sheath 122 and the introducer sheath 110, such as without limitation the constricted portion 113 of the main body 106 of the introducer 102 as discussed above, can form portions of the lumen through the catheter system 100.

In some embodiments, the outer sheath 122 can constrain or restrain an endoluminal prosthesis supported by the central tube 176 as described above. In this configuration, as the catheter tip 162, central core 154, and an endoluminal prosthesis (such as, but not limited to, stent 157 illustrated in FIGS. 7 and 12-14) are advanced through the outer sheath 122, the outer sheath 122 can restrain the endoluminal prosthesis and prevent the endoluminal prosthesis from expanding before reaching the target position within the patient's vasculature. Additionally, the catheter system 100 can be configured such that, as the catheter tip 162, central core 154, and endoluminal prosthesis are advanced past the distal end 122c of the outer sheath 122, the constricted portion 113 and, subsequently, the introducer sheath 110 can radially restrain the endoluminal prosthesis as the endoluminal prosthesis is advanced through the introducer sheath 110.

In some embodiments, the endoluminal prosthesis or the stent 157 can be a tubular stent, a bifurcated stent, or any other desirable stent, graft, stent graft, or endoluminal prosthesis (collectively referred to herein as stent or stents), including without limitation any of the stents or grafts disclosed in U.S. patent application Ser. No. 12/101,863 referenced above and incorporated herein by reference as if fully set forth herein. Accordingly, in some embodiments, the catheter system 100 or catheter 104 can be configured to deploy any suitable or desirable stent or stents.

Thus, in this configuration, the endoluminal prosthesis can be transferred from the outer sheath 122 to the introducer sheath 110. In this arrangement, using the introducer sheath 110 as the restraint can allow the outside diameter of the introducer sheath 110 to be reduced, which can minimize trauma to the patient's vasculature and assist in the deployment of the endoluminal prosthesis.

Many embodiments of the docking mechanism and catheter system have been described in connection with FIGS. 1-15. It will apparent to one of ordinary skill in the art that there are many potential embodiments of a permanent or removable docking mechanism that may be suitable for medical use and which are contemplated herein. For example, in some embodiments, a nut-screw combination could be used to connect the introducer sheath and the catheter. As another example, a bayonet style locking mechanism, such as is used for camera lenses, can also be used. In some embodiments, any of the components or features of some embodiments of the catheters disclosed herein or other catheters available in the field can be combined to form additional embodiments, all of which are contemplated herein.

While the above description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

What is claimed is:

1. A catheter system comprising:
   an introducer comprising a main body and a tubular introducer sheath projecting from the main body; and
   a catheter comprising a main body and an outer sheath projecting from the main body, the outer sheath configured to be at least partially advanced through the main body of the introducer;
   wherein the catheter is configured to engage with the introducer, and
   wherein the catheter further comprises an inner core that is configured to be advanceable through the main body of the catheter and the outer sheath;
   wherein the inner core is configured to be advanceable over a guidewire,
   wherein the introducer comprises a first seal portion, and
   wherein the first seal comprises a hemostasis valve and an annular rubber seal.

2. The catheter system of claim 1, wherein catheter is configured to be removably engaged with the introducer by axially locking the catheter to the introducer.

3. The catheter system of claim 1, wherein the wherein the first seal comprises an interference or close tolerance fit between the hemostasis valve and the annular rubber seal.

4. The catheter of claim 1, wherein the catheter retains multiple individual stent segments.

5. The catheter of claim 1, wherein the catheter retains a fenestrated stent or stent graft.

6. The catheter of claim 1, wherein the catheter retains a bifurcated stent or stent graft.

7. A method of placing a catheter into a blood vessel comprising:
   placing into a patient's vessel, an introducer comprising a main body and a tubular introducer sheath projecting from the main body; and
   passing a catheter through the introducer sheath,
   wherein the catheter comprises an inner core that is configured to be advanceable through the main body of the catheter, and
   wherein the inner core is configured to be advanceable over a guidewire,
   wherein the introducer comprises a first seal portion, and
   wherein the first seal comprises a hemostasis valve and an annular rubber seal.

8. The method of claim 7, wherein the catheter retains a stent or stent graft.

9. The method of claim 8, further comprising placing at least one stent or stent graft in the patient's blood vessel.

10. The method of claim 8, further comprising placing multiple stents or stent grafts in the patient's vessel.

11. The catheter system of claim 1, wherein the first seal comprises an interference or close tolerance fit between adjacent components.

12. A catheter system comprising:
an introducer comprising a main body and a tubular introducer sheath projecting from the main body; and
a catheter comprising a main body and an outer sheath projecting from the main body, the outer sheath configured to be at least partially advanced through the main body of the introducer;
wherein the catheter is configured to engage with the introducer, and
wherein the catheter further comprises an inner core that is configured to be advanceable through the main body of the catheter and the outer sheath;
wherein the inner core is configured to be advanceable over a guidewire; and
wherein the introducer comprises a first seal portion,
wherein the seal portion comprises an interference or close tolerance fit between adjacent components, wherein the adjacent components comprise at least two of the outer sheath, one or more inside surfaces of the main body, one or more inside surfaces of a hub portion of the introducer and the inner core.

13. The catheter system of claim 12, wherein the adjacent components comprise the outer sheath and one or more inside surfaces of the main body.

14. The catheter system of claim 12, wherein the adjacent components comprise the outer sheath and one or more inside surfaces of the hub portion of the introducer.

15. The catheter system of claim 12, wherein the adjacent components comprise the inner core and one or more inside surfaces of the main body.

16. The catheter system of claim 12, wherein the adjacent components comprise the inner core and one or more inside surfaces of the hub portion of the introducer.

* * * * *